US012685549B2

(12) United States Patent
Long et al.

(10) Patent No.: US 12,685,549 B2
(45) Date of Patent: Jul. 21, 2026

(54) CLOT TREATMENT SYSTEMS WITH DILATOR LOCKING MECHANISMS, AND ASSOCIATED DEVICES AND METHODS

(71) Applicant: STRYKER CORPORATION, Portage, MI (US)

(72) Inventors: Joshua Garrett Long, Mission Viejo, CA (US); Mikayla Ann Barkley, Newport Beach, CA (US); Benjamin Edward Merritt, San Clemente, CA (US)

(73) Assignee: Stryker Corporation, Portage, MI (US)

( * ) Notice: Subject to any disclaimer, the term of this patent is extended or adjusted under 35 U.S.C. 154(b) by 631 days.

(21) Appl. No.: 18/156,944

(22) Filed: Jan. 19, 2023

(65) Prior Publication Data

US 2023/0248380 A1 Aug. 10, 2023

Related U.S. Application Data

(60) Provisional application No. 63/307,766, filed on Feb. 8, 2022.

(51) Int. Cl.
A61B 17/221 (2006.01)
A61M 25/00 (2006.01)

(52) U.S. Cl.
CPC ....... A61B 17/221 (2013.01); A61M 25/0075 (2013.01)

(58) Field of Classification Search
CPC ...... A61B 17/29; A61B 17/221; A61M 29/00; A61M 29/02; A61M 2029/025;
(Continued)

(56) References Cited

U.S. PATENT DOCUMENTS 1,101,890 A 6/1914 Tunstead
2,434,835 A 1/1948 Colley
(Continued)

FOREIGN PATENT DOCUMENTS

AU 2015210338 8/2015
AU 2016202497 5/2016
(Continued)

OTHER PUBLICATIONS

US 12,114,876 B2, 10/2024, Quick et al. (withdrawn)
(Continued)

*Primary Examiner* — Kankindi Rwego
(74) *Attorney, Agent, or Firm* — Perkins Coie LLP

(57) ABSTRACT

Disclosed herein are vascular access systems with dilator locking mechanisms, and associated devices and methods. In some embodiments, the dilator locking mechanisms include a first cap coupled to a dilator component and a second cap coupled to the vascular access system. The first cap can include one or more locking members. The second cap can include one or more locking features, each configured to be releasably coupled to one of the locking members. In operation, the dilator component can be inserted into the vascular access system, and at least a portion of one or more of the locking members can be aligned with and inserted into the corresponding locking feature to, e.g., couple the first cap and the second cap. The interaction between first and second caps when coupled can at least partially prevent the dilator from moving relative to the vascular access system.

32 Claims, 10 Drawing Sheets

(58) Field of Classification Search
CPC .......... A61M 25/0075; A61M 25/0074; A61M
2025/0076; A61M 2025/0078; A61M
2025/0079
USPC ................................................. 606/191, 159
See application file for complete search history.

(56) References Cited

U.S. PATENT DOCUMENTS

| | | | |
|---|---|---|---|
| 2,502,639 A | 4/1950 | Blake |
| 2,695,023 A | 11/1954 | Brown |
| 2,707,954 A | 5/1955 | Kas, Sr. |
| 2,784,717 A | 3/1957 | Thompson |
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,383,131 A | 5/1968 | Rosfelder |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,661,144 A | 5/1972 | Jensen et al. |
| 3,675,657 A | 7/1972 | Gauthier |
| 3,785,380 A | 1/1974 | Brumfield |
| 3,860,006 A | 1/1975 | Patel |
| 3,863,624 A | 2/1975 | Gram |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,036,232 A | 7/1977 | Genese |
| 4,187,849 A | 2/1980 | Stim |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,693,257 A | 9/1987 | Markham |
| 4,705,518 A | 11/1987 | Baker et al. |
| 4,743,230 A | 5/1988 | Nordquest |
| 4,776,337 A | 10/1988 | Palmaz |
| 4,790,812 A | 12/1988 | Hawkins, Jr. et al. |
| 4,826,483 A | 5/1989 | Molnar, IV |
| 4,863,440 A | 9/1989 | Chin et al. |
| 4,870,953 A | 10/1989 | DonMichael et al. |
| 4,872,579 A | 10/1989 | Palmer |
| 4,880,408 A | 11/1989 | Cumes et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,053,008 A | 10/1991 | Bajaj |
| 5,059,178 A | 10/1991 | Ya |
| 5,064,428 A | 11/1991 | Cope et al. |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,156,594 A | 10/1992 | Keith |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,201,707 A | 4/1993 | Kanai |
| 5,215,536 A | 6/1993 | Lampropoulos et al. |
| 5,234,403 A | 8/1993 | Yoda et al. |
| 5,242,461 A | 9/1993 | Kortenbach et al. |
| 5,244,619 A | 9/1993 | Burnham |
| 5,246,011 A | 9/1993 | Caillouette |
| 5,250,025 A | 10/1993 | Sosnowski et al. |
| 5,279,546 A | 1/1994 | Mische et al. |
| 5,323,514 A | 6/1994 | Masuda et al. |
| 5,329,923 A | 7/1994 | Lundquist |
| 5,337,780 A | 8/1994 | Kee |
| 5,360,417 A | 11/1994 | Gravener et al. |
| 5,364,345 A | 11/1994 | Lowery et al. |
| 5,370,624 A | 12/1994 | Edwards et al. |
| 5,376,071 A | 12/1994 | Henderson |
| 5,376,101 A | 12/1994 | Green et al. |
| 5,378,230 A | 1/1995 | Mahurkar |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,429,610 A | 7/1995 | Vaillancourt |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,867,385 A | 2/1999 | Brown et al. |
| 5,873,866 A | 2/1999 | Kondo et al. |
| 5,873,882 A | 2/1999 | Straub et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,728 A | 6/1999 | Sepetka et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,951,539 A | 9/1999 | Nita et al. |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,036,717 A | 3/2000 | Mers Kelly |
| 6,059,745 A | 5/2000 | Gelbfish |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |

(56) References Cited

U.S. PATENT DOCUMENTS

| | | | |
|---|---|---|---|
| 6,146,403 A | 11/2000 | St. Germain |
| 6,152,144 A | 11/2000 | Lesh et al. |
| 6,152,909 A | 11/2000 | Bagaoisan et al. |
| 6,152,946 A | 11/2000 | Broome et al. |
| 6,156,046 A | 12/2000 | Passafaro et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,809 B1 | 1/2001 | Khairkhahan et al. |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,383,206 B1 | 5/2002 | Gillick |
| 6,398,756 B2 | 6/2002 | Peterson |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,436,085 B1 | 8/2002 | Lauer |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,511,496 B1 | 1/2003 | Huter |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,558,405 B1 | 5/2003 | Mcinnes |
| 6,564,828 B1 | 5/2003 | Ishida |
| 6,569,181 B1 | 5/2003 | Burns |
| 6,575,995 B1 | 6/2003 | Huter et al. |
| 6,575,996 B1 | 6/2003 | Denison |
| 6,589,263 B1 | 7/2003 | Hopkins et al. |
| 6,589,264 B1 | 7/2003 | Barbut et al. |
| 6,592,616 B1 | 7/2003 | Stack |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,220 B1 | 11/2003 | Huter |
| 6,645,222 B1 | 11/2003 | Parodi et al. |
| 6,645,223 B2 | 11/2003 | Boyle |
| 6,652,548 B2 | 11/2003 | Evans et al. |
| 6,656,202 B2 | 12/2003 | Papp |
| 6,656,351 B2 | 12/2003 | Boyle |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,679,893 B1 | 1/2004 | Tran |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 | 6/2005 | Hajianpour |
| 6,929,652 B1 | 8/2005 | Andrews |
| 6,939,361 B1 | 9/2005 | Kleshinski |
| 6,939,362 B2 | 9/2005 | Boyle |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,004,955 B2 | 2/2006 | Shen |
| 7,004,956 B2 | 2/2006 | Palmer |
| 7,036,707 B2 | 5/2006 | Aota et al. |
| 7,041,084 B2 | 5/2006 | Fotjik |
| 7,048,758 B2 | 5/2006 | Boyle |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,097,651 B2 | 8/2006 | Harrison |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,172,614 B2 | 2/2007 | Boyle |
| 7,179,273 B1 | 2/2007 | Palmer et al. |
| 7,217,255 B2 | 5/2007 | Boyle |
| 7,223,253 B2 | 5/2007 | Hogendijk |
| 7,232,432 B2 | 6/2007 | Fulton, III et al. |
| 7,241,304 B2 | 7/2007 | Boyle |
| 7,244,243 B2 | 7/2007 | Lary |
| 7,252,675 B2 | 8/2007 | Denison |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,973 B2 | 2/2008 | Gesswein |
| 7,331,980 B2 | 2/2008 | Dubrul et al. |
| 7,338,510 B2 | 3/2008 | Boylan |
| 7,344,549 B2 | 3/2008 | Boyle |
| 7,425,215 B2 | 9/2008 | Boyle |
| 7,481,805 B2 | 1/2009 | Magnusson |
| 7,534,234 B2 | 5/2009 | Fotjik |
| 7,544,202 B2 | 6/2009 | Cartier |
| 7,578,830 B2 | 8/2009 | Kusleika et al. |
| 7,621,870 B2 | 11/2009 | Berrada et al. |
| 7,662,166 B2 | 2/2010 | Boyle |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 | 11/2010 | Nieoson et al. |
| 7,879,065 B2 | 2/2011 | Gesswein |
| 7,905,877 B1 | 3/2011 | Oscar et al. |
| 7,905,896 B2 | 3/2011 | Straub |

(56)  References Cited

U.S. PATENT DOCUMENTS

| | | |
|---|---|---|
| 7,938,809 B2 | 5/2011 | Lampropoulos et al. |
| 7,938,820 B2 | 5/2011 | Webster et al. |
| 7,942,892 B2 | 5/2011 | D'Aquanni et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krollk et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,275 B2 | 2/2012 | Mialhe |
| 8,118,829 B2 | 2/2012 | Carrison et al. |
| 8,187,465 B2 | 5/2012 | Nierich |
| 8,191,457 B2 | 6/2012 | Kanner et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,262,689 B2 | 9/2012 | Schneiderman |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,366,737 B2 | 2/2013 | Hancock |
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,496,653 B2 | 7/2013 | Steinke |
| 8,512,352 B2 | 8/2013 | Martin |
| 8,523,897 B2 | 9/2013 | van der Burg et al. |
| 8,529,596 B2 | 9/2013 | Grandfield et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,591,540 B2 | 11/2013 | Boyle |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,641,777 B2 | 2/2014 | Strauss |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,764,730 B2 | 7/2014 | Taber |
| 8,771,289 B2 | 7/2014 | Mohluddin et al. |
| 8,777,893 B2 | 7/2014 | Malewicz |
| 8,777,976 B2 | 7/2014 | Brady |
| 8,784,434 B2 | 7/2014 | Rosenbluth |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,882,797 B2 | 11/2014 | Janardhan |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,023,077 B2 | 5/2015 | Cully |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,358,037 B2 | 6/2016 | Farhangnia et al. |
| 9,402,938 B2 | 8/2016 | Aklog et al. |
| 9,439,664 B2 | 9/2016 | Sos |
| 9,439,751 B2 | 9/2016 | White et al. |
| 9,445,828 B2 | 9/2016 | Turjman |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,693,852 B2 | 7/2017 | Lam |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |

(56) References Cited

U.S. PATENT DOCUMENTS

| | | | |
|---|---|---|---|
| 9,844,387 | B2 | 12/2017 | Marchand et al. |
| 9,844,643 | B2 | 12/2017 | Beasley et al. |
| 9,848,975 | B2 | 12/2017 | Hauser |
| 9,849,014 | B2 | 12/2017 | Kusleika |
| 9,884,387 | B2 | 2/2018 | Plha |
| 9,931,495 | B2 | 4/2018 | Aboytes |
| 9,937,321 | B2 | 4/2018 | Welch et al. |
| 9,962,178 | B2 | 5/2018 | Greenhalgh et al. |
| 9,980,813 | B2 | 5/2018 | Eller |
| 9,999,493 | B2 | 6/2018 | Nguyen et al. |
| 10,004,531 | B2 | 6/2018 | Rosenbluth et al. |
| 10,010,335 | B2 | 7/2018 | Greenhalgh et al. |
| 10,016,206 | B1 | 7/2018 | Yang |
| 10,016,266 | B2 | 7/2018 | Hauser |
| 10,016,532 | B2 | 7/2018 | Zhang |
| 10,028,759 | B2 | 7/2018 | Wallace et al. |
| 10,045,790 | B2 | 8/2018 | Cox et al. |
| 10,058,339 | B2 | 8/2018 | Galdonik et al. |
| 10,098,651 | B2 | 10/2018 | Marchand et al. |
| 10,117,974 | B2 | 11/2018 | Li |
| 10,130,379 | B2 | 11/2018 | Welch |
| 10,130,385 | B2 | 11/2018 | Farhangnia et al. |
| 10,130,795 | B2 | 11/2018 | Parhangnia et al. |
| 10,179,224 | B2 | 1/2019 | Yang et al. |
| 10,183,147 | B2 | 1/2019 | Yang et al. |
| 10,183,159 | B2 | 1/2019 | Nobles et al. |
| 10,188,829 | B2 | 1/2019 | Beasley et al. |
| 10,195,320 | B2 | 2/2019 | Fisher et al. |
| 10,226,263 | B2 | 3/2019 | Look et al. |
| 10,238,406 | B2 | 3/2019 | Cox et al. |
| 10,271,863 | B2 | 4/2019 | Marks |
| 10,271,864 | B2 | 4/2019 | Greenhalgh et al. |
| 10,327,883 | B2 | 6/2019 | Yachia |
| 10,335,186 | B2 | 7/2019 | Rosenbluth et al. |
| 10,342,571 | B2 | 7/2019 | Marchand et al. |
| 10,349,960 | B2 | 7/2019 | Quick |
| 10,363,054 | B2 | 7/2019 | Vale |
| 10,383,644 | B2 | 8/2019 | Molael et al. |
| 10,383,983 | B2 | 8/2019 | Aklog et al. |
| 10,384,034 | B2 | 8/2019 | Carrison et al. |
| 10,426,510 | B2 | 10/2019 | Farhangnia et al. |
| 10,426,511 | B2 | 10/2019 | Hehrlein |
| 10,426,644 | B2 | 10/2019 | Shrivastava et al. |
| 10,441,745 | B2 | 10/2019 | Yang et al. |
| 10,448,969 | B2 | 10/2019 | Sutton |
| 10,456,151 | B2 | 10/2019 | Slee et al. |
| 10,456,159 | B2 | 10/2019 | Vetter |
| 10,456,555 | B2 | 10/2019 | Carrison et al. |
| 10,471,234 | B2 | 11/2019 | Taber |
| 10,478,535 | B2 | 11/2019 | Ogle |
| 10,485,952 | B2 | 11/2019 | Carrison et al. |
| 10,492,805 | B2 | 12/2019 | Culbert et al. |
| 10,524,811 | B2 | 1/2020 | Marchand et al. |
| 10,531,883 | B1 | 1/2020 | Deville et al. |
| 10,537,710 | B2 | 1/2020 | Jalgaonkar et al. |
| 10,561,440 | B2 | 2/2020 | Look et al. |
| 10,588,655 | B2 | 3/2020 | Rosenbluth et al. |
| 10,648,268 | B2 | 5/2020 | Jaffrey et al. |
| 10,661,053 | B2 | 5/2020 | Yang et al. |
| 10,695,159 | B2 | 6/2020 | Hauser |
| 10,709,471 | B2 | 7/2020 | Rosenbluth et al. |
| 10,716,880 | B2 | 7/2020 | Culbert et al. |
| 10,729,455 | B2 | 8/2020 | Goyal et al. |
| 10,743,907 | B2 | 8/2020 | Bruzzi et al. |
| 10,772,636 | B2 | 9/2020 | Kassab et al. |
| 10,779,852 | B2 | 9/2020 | Bruzzi et al. |
| 10,779,855 | B2 | 9/2020 | Garrison |
| 10,792,056 | B2 | 10/2020 | Vale et al. |
| 10,799,331 | B2 | 10/2020 | Hauser |
| 10,799,671 | B2 | 10/2020 | Shimada et al. |
| 10,806,559 | B2 | 10/2020 | Bonnette |
| 10,813,663 | B2 | 10/2020 | Bruzzi et al. |
| 10,828,061 | B2 | 11/2020 | Bonnette et al. |
| 10,835,269 | B1 | 11/2020 | Wallace |
| 10,835,711 | B2 | 11/2020 | Yang et al. |
| 10,874,421 | B2 | 12/2020 | Bruzzi et al. |
| 10,912,577 | B2 | 2/2021 | Marchand et al. |
| 10,926,060 | B2 | 2/2021 | Stern et al. |
| 10,939,932 | B1 | 3/2021 | Yang |
| 10,953,195 | B2 | 3/2021 | Jalgaonkar et al. |
| 10,960,114 | B2 | 3/2021 | Goisis |
| 10,967,111 | B2 | 4/2021 | Iida |
| 10,994,059 | B2 | 5/2021 | Moore |
| 10,994,063 | B2 | 5/2021 | Fisher et al. |
| 11,000,357 | B2 | 5/2021 | Ashkenazi |
| 11,000,682 | B2 | 5/2021 | Merritt et al. |
| 11,013,523 | B2 | 5/2021 | Arad Hadar |
| 11,058,445 | B2 | 7/2021 | Cox et al. |
| 11,058,451 | B2 | 7/2021 | Marchand et al. |
| 11,065,019 | B1 | 7/2021 | Chou et al. |
| 11,065,028 | B2 | 7/2021 | Parhangnia et al. |
| 11,147,571 | B2 | 10/2021 | Cox et al. |
| 11,147,948 | B2 | 10/2021 | Beasley et al. |
| 11,147,949 | B2 | 10/2021 | Yang et al. |
| 11,154,314 | B2 | 10/2021 | Quick |
| 11,166,703 | B2 | 11/2021 | Kassab et al. |
| 11,185,664 | B2 | 11/2021 | Carrison et al. |
| 11,197,684 | B1 | 12/2021 | Ngo et al. |
| 11,213,356 | B2 | 1/2022 | Tanner et al. |
| 11,224,450 | B2 | 1/2022 | Chou et al. |
| 11,224,721 | B2 | 1/2022 | Carrison et al. |
| 11,253,277 | B2 | 2/2022 | Buck et al. |
| 11,259,821 | B2 | 3/2022 | Buck et al. |
| 11,266,825 | B2 | 3/2022 | Peter et al. |
| 11,278,307 | B2 | 3/2022 | Bruzzi et al. |
| 11,304,713 | B2 | 4/2022 | Hansen |
| 11,305,094 | B2 | 4/2022 | Carrison et al. |
| 11,317,939 | B2 | 5/2022 | Bruzzi et al. |
| 11,337,714 | B2 | 5/2022 | Ferrera et al. |
| 11,376,028 | B1 | 7/2022 | Saadat |
| 11,382,733 | B2 | 7/2022 | Eli |
| 11,383,064 | B2 | 7/2022 | Carrison et al. |
| 11,395,903 | B2 | 7/2022 | Carrison et al. |
| 11,406,418 | B2 | 8/2022 | Bruzzi et al. |
| 11,419,621 | B2 | 8/2022 | Goyal et al. |
| 11,433,218 | B2 | 9/2022 | Quick et al. |
| 11,439,799 | B2 | 9/2022 | Buck et al. |
| 11,457,936 | B2 | 10/2022 | Buck et al. |
| 11,478,262 | B2 | 10/2022 | Ngo et al. |
| 11,529,158 | B2 | 12/2022 | Hauser |
| 11,541,184 | B2 | 1/2023 | Han et al. |
| 11,553,935 | B2 | 1/2023 | Buck et al. |
| 11,553,942 | B2 | 1/2023 | Bonnette et al. |
| 11,554,005 | B2 | 1/2023 | Merritt et al. |
| 11,559,382 | B2 | 1/2023 | Merritt et al. |
| 11,576,691 | B2 | 2/2023 | Chou et al. |
| 11,589,880 | B2 | 2/2023 | Aklog et al. |
| 11,596,768 | B2 | 3/2023 | Stern et al. |
| 11,607,483 | B2 | 3/2023 | Iida |
| 11,633,272 | B2 | 4/2023 | Buck et al. |
| 11,638,637 | B2 | 5/2023 | Buck et al. |
| 11,642,209 | B2 | 5/2023 | Merritt et al. |
| 11,648,028 | B2 | 5/2023 | Rosenbluth et al. |
| 11,672,561 | B2 | 6/2023 | Look et al. |
| 11,678,905 | B2 | 6/2023 | Look et al. |
| 11,697,011 | B2 | 7/2023 | Merritt et al. |
| 11,697,012 | B2 | 7/2023 | Merritt et al. |
| 11,724,052 | B2 | 8/2023 | White et al. |
| 11,730,925 | B2 | 8/2023 | Saadat et al. |
| 11,744,691 | B2 | 9/2023 | Merritt et al. |
| 11,806,033 | B2 | 11/2023 | Marchand et al. |
| 11,819,228 | B2 | 11/2023 | Buck et al. |
| 11,832,837 | B2 | 12/2023 | Hauser |
| 11,832,838 | B2 | 12/2023 | Hauser |
| 11,833,023 | B2 | 12/2023 | Hauser |
| 11,839,393 | B2 | 12/2023 | Hauser |
| 11,844,921 | B2 | 12/2023 | Merritt et al. |
| 11,849,963 | B2 | 12/2023 | Quick |
| 11,865,291 | B2 | 1/2024 | Merritt et al. |
| 11,890,180 | B2 | 2/2024 | Merritt et al. |
| 11,918,243 | B2 | 3/2024 | Marchand et al. |
| 11,918,244 | B2 | 3/2024 | Marchand et al. |
| 11,925,369 | B2 | 3/2024 | Hauser |
| 11,937,834 | B2 | 3/2024 | Dinh |

(56) References Cited

U.S. PATENT DOCUMENTS

| | | |
|---|---|---|
| 11,937,838 B2 | 3/2024 | Cox et al. |
| 11,963,861 B2 | 4/2024 | Strauss et al. |
| 11,969,178 B2 | 4/2024 | Hauser |
| 11,969,331 B2 | 4/2024 | Merritt et al. |
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,537 B2 | 5/2024 | Merritt et al. |
| 11,986,382 B2 | 5/2024 | Merritt et al. |
| 11,998,436 B2 | 6/2024 | Merritt et al. |
| 12,016,580 B2 | 6/2024 | Quick et al. |
| 12,023,057 B2 | 7/2024 | Hauser |
| 12,102,343 B2 | 10/2024 | Quick |
| 12,109,384 B2 | 10/2024 | Merritt et al. |
| 12,156,669 B2 | 12/2024 | Quick et al. |
| 12,239,333 B2 | 3/2025 | Quick et al. |
| 12,251,120 B2 | 3/2025 | Marchand et al. |
| 12,274,459 B2 | 4/2025 | Dihn |
| 12,310,608 B2 | 5/2025 | Marchand et al. |
| 12,343,028 B2 | 7/2025 | Cox et al. |
| 12,364,496 B2 | 7/2025 | Scheinblum et al. |
| 12,465,382 B1 | 11/2025 | Merritt et al. |
| 2001/0004699 A1 | 6/2001 | Gittings et al. |
| 2001/0031981 A1 | 10/2001 | Evans et al. |
| 2001/0041881 A1 | 11/2001 | Sarge et al. |
| 2001/0041909 A1 | 11/2001 | Tsugita et al. |
| 2001/0049486 A1 | 12/2001 | Evans et al. |
| 2001/0049517 A1 | 12/2001 | Zadno-azizi et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0058910 A1 | 5/2002 | Hermann et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0165536 A1 | 11/2002 | Kelley et al. |
| 2002/0169474 A1 | 11/2002 | Kusleika |
| 2002/0173812 A1 | 11/2002 | McGuckin, Jr. et al. |
| 2002/0173819 A1 | 11/2002 | Leeflang et al. |
| 2002/0188276 A1 | 12/2002 | Evans et al. |
| 2003/0004536 A1 | 1/2003 | Boylan et al. |
| 2003/0023263 A1 | 1/2003 | Krolik et al. |
| 2003/0069601 A1 | 4/2003 | Nowakowski et al. |
| 2003/0083693 A1 | 5/2003 | Daniel et al. |
| 2003/0093106 A1 | 5/2003 | Brady et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0144672 A1 | 7/2003 | Gellman et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191425 A1 | 10/2003 | Rosenblatt et al. |
| 2003/0191516 A1 | 10/2003 | Weldon et al. |
| 2003/0208224 A1 | 11/2003 | Broome |
| 2003/0216774 A1 | 11/2003 | Larson |
| 2003/0225379 A1 | 12/2003 | Schaffer et al. |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0204738 A1 | 10/2004 | Weber et al. |
| 2004/0260331 A1 | 12/2004 | D'Aquanni et al. |
| 2004/0260333 A1 | 12/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0080398 A1 | 4/2005 | Markel et al. |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0131387 A1 | 6/2005 | Pursley |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0256452 A1 | 11/2005 | DeMarchi et al. |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0079787 A1 | 4/2006 | Whiting et al. |
| 2006/0085952 A1 | 4/2006 | Kaneko et al. |
| 2006/0089533 A1 | 4/2006 | Ziegler et al. |
| 2006/0100662 A1 | 5/2006 | Daniel et al. |
| 2006/0136043 A1 | 6/2006 | Cully et al. |
| 2006/0142694 A1 | 6/2006 | Bednarek et al. |
| 2006/0149219 A1 | 7/2006 | Calderon |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0060911 A1 | 3/2007 | Webster et al. |
| 2007/0088382 A1 | 4/2007 | Bei |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |

(56) References Cited

U.S. PATENT DOCUMENTS

| | | |
|---|---|---|
| 2008/0033467 A1 | 2/2008 | Miyamoto et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018550 A1 | 1/2009 | Poll |
| 2009/0018566 A1 | 1/2009 | Escudero et al. |
| 2009/0043372 A1 | 2/2009 | Northrop et al. |
| 2009/0054918 A1 | 2/2009 | Henson |
| 2009/0062602 A1 | 3/2009 | Rosenberg et al. |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0049225 A1 | 2/2010 | To et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0094320 A1 | 4/2010 | Arat |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai |
| 2010/0190156 A1 | 7/2010 | Van Wordragen et al. |
| 2010/0204712 A1 | 8/2010 | Mallaby |
| 2010/0217261 A1 | 8/2010 | Watson |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0297577 A1 | 11/2010 | Cohen |
| 2010/0318178 A1 | 12/2010 | Rapaport et al. |
| 2010/0331776 A1 | 12/2010 | Salahieh et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1 | 4/2011 | Sibbitt, Jr. et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0116440 A1 | 5/2012 | Leynov et al. |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1* | 5/2013 | Holm ................... A61M 29/00 604/171 |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0172851 A1 | 7/2013 | Shimada et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0046297 A1 | 2/2014 | Shimada et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0135736 A1 | 5/2014 | Hebert |
| 2014/0155830 A1 | 6/2014 | Bonnette et al. |
| 2014/0155908 A1 | 6/2014 | Rosenbluth et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |

(56)         References Cited

U.S. PATENT DOCUMENTS

| | | |
|---|---|---|
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0119862 A1 | 4/2015 | Cajamarca et al. |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0283309 A1 | 10/2015 | Look et al. |
| 2015/0305756 A1 | 10/2015 | Rosenbluth |
| 2015/0305759 A1 | 10/2015 | St. George et al. |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0359547 A1 | 12/2015 | Vale et al. |
| 2015/0360001 A1 | 12/2015 | Quick |
| 2015/0366690 A1 | 12/2015 | Lumauig |
| 2015/0374391 A1 | 12/2015 | Quick |
| 2016/0008014 A1 | 1/2016 | Rosenbluth |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0067450 A1 | 3/2016 | Kowshik |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0250406 A1 | 9/2016 | Parisotto et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0035445 A1 | 2/2017 | Nguyen et al. |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112513 A1 | 4/2017 | Marchand et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0165468 A1 | 6/2017 | Nobles et al. |
| 2017/0172591 A1 | 6/2017 | Ulm, III |
| 2017/0189041 A1 | 7/2017 | Cox et al. |
| 2017/0196576 A1 | 7/2017 | Long et al. |
| 2017/0203076 A1 | 7/2017 | Groneberg et al. |
| 2017/0209162 A1 | 7/2017 | Sperry et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0252536 A1 | 9/2017 | Yang et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0319776 A1 | 11/2017 | Eisner et al. |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0014840 A1 | 1/2018 | Panian |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0049873 A1 | 2/2018 | Manash et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0071490 A1 | 3/2018 | Khuu et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1 | 8/2018 | Fields et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0264230 A1 | 9/2018 | Funk et al. |
| 2018/0280623 A1 | 10/2018 | Pilkington et al. |
| 2018/0289394 A1 | 10/2018 | Shah |
| 2018/0296240 A1 | 10/2018 | Rosenbluth et al. |
| 2018/0296798 A1 | 10/2018 | Kepak et al. |
| 2018/0296801 A1 | 10/2018 | Tegg et al. |
| 2018/0304040 A1 | 10/2018 | Jalgaonkar et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0344981 A1 | 12/2018 | Laduca et al. |
| 2018/0353195 A1 | 12/2018 | Sigmon, Jr. et al. |
| 2018/0353668 A1 | 12/2018 | Meyer et al. |

(56)  References Cited

U.S. PATENT DOCUMENTS

| | | |
|---|---|---|
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0216476 A1 | 7/2019 | Barry et al. |
| 2019/0223893 A1 | 7/2019 | Gilvarry et al. |
| 2019/0231372 A1 | 8/2019 | Brady |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0328411 A1 | 10/2019 | Vale et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2019/0366049 A1 | 12/2019 | Hannon et al. |
| 2019/0374239 A1 | 12/2019 | Martin et al. |
| 2020/0009301 A1 | 1/2020 | Yee |
| 2020/0022711 A1 | 1/2020 | Look et al. |
| 2020/0030579 A1 | 1/2020 | Taber |
| 2020/0046368 A1 | 2/2020 | Merritt et al. |
| 2020/0046940 A1 | 2/2020 | Carrison et al. |
| 2020/0054861 A1 | 2/2020 | Korkuch et al. |
| 2020/0060802 A1 | 2/2020 | Hamill et al. |
| 2020/0069889 A1 | 3/2020 | Lin |
| 2020/0078029 A1 | 3/2020 | Hansen et al. |
| 2020/0113412 A1 | 4/2020 | Jensen |
| 2020/0121334 A1 | 4/2020 | Galdonik et al. |
| 2020/0129741 A1 | 4/2020 | Kawwas et al. |
| 2020/0187596 A1 | 6/2020 | Krout et al. |
| 2020/0222666 A1 | 7/2020 | Chan et al. |
| 2020/0246029 A1 | 8/2020 | Singleton |
| 2020/0297376 A1 | 9/2020 | Marks |
| 2020/0324079 A1 | 10/2020 | Jalgaonkar et al. |
| 2020/0375616 A1 | 12/2020 | Fitz |
| 2020/0397452 A1 | 12/2020 | Twomey |
| 2021/0022766 A1 | 1/2021 | Bruzzi et al. |
| 2021/0022843 A1 | 1/2021 | Hauser |
| 2021/0038385 A1 | 2/2021 | Popp et al. |
| 2021/0069468 A1 | 3/2021 | Keating et al. |
| 2021/0113224 A1 | 4/2021 | Dinh |
| 2021/0128182 A1 | 5/2021 | Teigen et al. |
| 2021/0128184 A1 | 5/2021 | Fulkerson et al. |
| 2021/0128185 A1 | 5/2021 | Nguyen et al. |
| 2021/0137667 A1 | 5/2021 | Sonnette et al. |
| 2021/0138193 A1 | 5/2021 | Garrison et al. |
| 2021/0138194 A1 | 5/2021 | Carrison et al. |
| 2021/0153884 A1 | 5/2021 | Casey |
| 2021/0154433 A1 | 5/2021 | Casey et al. |
| 2021/0186537 A1 | 6/2021 | Buck et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0251757 A1 | 8/2021 | Siegel et al. |
| 2021/0275197 A1 | 9/2021 | Vale |
| 2021/0290925 A1 | 9/2021 | Merritt et al. |
| 2021/0315596 A1 | 10/2021 | Buck et al. |
| 2021/0315598 A1 | 10/2021 | Buck et al. |
| 2021/0316127 A1 | 10/2021 | Buck et al. |
| 2021/0322166 A1 | 10/2021 | von Oepen et al. |
| 2021/0330344 A1 | 10/2021 | Rosenbluth et al. |
| 2021/0338984 A1 | 11/2021 | Booker et al. |
| 2021/0361428 A1 | 11/2021 | Dixon |
| 2021/0378648 A1 | 12/2021 | Thissen et al. |
| 2021/0378692 A1 | 12/2021 | Xiang et al. |
| 2021/0378694 A1 | 12/2021 | Thress et al. |
| 2021/0393276 A1 | 12/2021 | Whelan |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015784 A1 | 1/2022 | Erlick |
| 2022/0015798 A1 | 1/2022 | Marchand et al. |
| 2022/0021197 A1 | 1/2022 | Zhao et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0047281 A1 | 2/2022 | Kamalova |
| 2022/0125451 A1 | 4/2022 | Hauser |
| 2022/0126060 A1 | 4/2022 | Shia et al. |
| 2022/0142638 A1 | 5/2022 | Enright et al. |
| 2022/0151647 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0226555 A1 | 7/2022 | Sunenshine et al. |
| 2022/0240959 A1 | 8/2022 | Quick |
| 2022/0265964 A1 | 8/2022 | Asami et al. |
| 2022/0288356 A1 | 9/2022 | Hiorth et al. |
| 2022/0296797 A1 | 9/2022 | Chawla |
| 2022/0330961 A1 | 10/2022 | Akpinar |
| 2022/0331554 A1 | 10/2022 | Beasley et al. |
| 2022/0346800 A1 | 11/2022 | Merritt et al. |
| 2022/0346801 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2022/0378445 A1 | 12/2022 | Culbert et al. |
| 2022/0378446 A1 | 12/2022 | Culbert et al. |
| 2022/0378447 A1 | 12/2022 | Culbert et al. |
| 2022/0378448 A1 | 12/2022 | Culbert et al. |
| 2022/0378451 A1 | 12/2022 | Goyal et al. |
| 2022/0378460 A1 | 12/2022 | Culbert et al. |
| 2022/0387072 A1 | 12/2022 | Look et al. |
| 2023/0015259 A1 | 1/2023 | Buck et al. |
| 2023/0047682 A1 | 2/2023 | Deaton et al. |
| 2023/0052964 A1 | 2/2023 | Singh et al. |
| 2023/0059721 A1 | 2/2023 | Chou et al. |
| 2023/0062809 A1 | 3/2023 | Merritt et al. |
| 2023/0063701 A1 | 3/2023 | Horowitz et al. |
| 2023/0070120 A1 | 3/2023 | Cox et al. |
| 2023/0122587 A1 | 4/2023 | Chou et al. |
| 2023/0145569 A1 | 5/2023 | McWeeney et al. |
| 2023/0149034 A1 | 5/2023 | Aklog et al. |
| 2023/0181200 A1 | 6/2023 | Deville et al. |
| 2023/0200970 A1 | 6/2023 | Merritt et al. |
| 2023/0210554 A1 | 7/2023 | Bruzzi et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355256 A1 | 11/2023 | Dinh |

(56) References Cited

U.S. PATENT DOCUMENTS

| | | | |
|---|---|---|---|
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0074771 A1 | 3/2024 | Quick et al. |
| 2024/0081857 A1 | 3/2024 | Luong et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |
| 2024/0407905 A1 | 12/2024 | Merrit et al. |
| 2024/0415626 A1 | 12/2024 | Merrit et al. |
| 2024/0415627 A1 | 12/2024 | Merrit et al. |
| 2025/0017618 A1 | 1/2025 | Truty et al. |
| 2025/0049456 A1 | 2/2025 | Cox et al. |
| 2025/0064464 A1 | 2/2025 | Barkley et al. |
| 2025/0090182 A1 | 3/2025 | Slaughter et al. |
| 2025/0161572 A1 | 5/2025 | Zikry et al. |
| 2025/0177625 A1 | 6/2025 | Merritt |
| 2025/0281192 A1 | 9/2025 | Quick et al. |
| 2025/0302496 A1 | 10/2025 | Marchand et al. |
| 2025/0318843 A1 | 10/2025 | Dinh et al. |
| 2025/0318846 A1 | 10/2025 | Marchand et al. |
| 2025/0318847 A1 | 10/2025 | Scheinblum et al. |
| 2025/0325291 A1 | 10/2025 | Quick |
| 2025/0325794 A1 | 10/2025 | Merritt et al. |
| 2025/0325795 A1 | 10/2025 | Merritt et al. |
| 2025/0345080 A1 | 11/2025 | Merritt et al. |

FOREIGN PATENT DOCUMENTS

| | | |
|---|---|---|
| AU | 2015218421 | 8/2017 |
| BR | PI0809253 | 9/2014 |
| CN | 1501825 | 6/2004 |
| CN | 102014772 | 4/2011 |
| CN | 102186427 | 9/2011 |
| CN | 102316809 | 1/2012 |
| CN | 103764049 | 4/2014 |
| CN | 103932756 | 7/2014 |
| CN | 104068910 | 10/2014 |
| CN | 105663841 | 6/2016 |
| CN | 106178227 | 12/2016 |
| CN | 106470728 | 3/2017 |
| CN | 106999271 | 8/2017 |
| CN | 108348319 | 7/2018 |
| CN | 110312481 | 10/2019 |
| CN | 110420046 | 11/2019 |
| CN | 110652645 | 1/2020 |
| CN | 111281482 | 6/2020 |
| CN | 112168286 | 1/2021 |
| CN | 112494102 | 3/2021 |
| CN | 112888384 | 6/2021 |
| CN | 214017710 | 8/2021 |
| CN | 113423348 | 9/2021 |
| CN | 113440217 | 9/2021 |
| CN | 215082793 | 12/2021 |
| CN | 215349271 | 12/2021 |
| CN | 114246639 | 3/2022 |
| CN | 215960137 | 3/2022 |
| CN | 216148140 | 4/2022 |
| CN | 114502086 | 5/2022 |
| DE | 1116001 | 10/1961 |
| DE | 102017004383 | 7/2018 |
| EP | 0432897 | 2/1996 |
| EP | 0914807 | 5/1999 |
| EP | 0956072 | 10/2001 |
| EP | 1254634 | 11/2002 |
| EP | 1663086 | 6/2006 |
| EP | 1267952 | 7/2008 |
| EP | 1937348 | 7/2008 |
| EP | 1991138 | 11/2008 |
| EP | 2073864 | 7/2009 |
| EP | 2203209 | 7/2010 |
| EP | 2209509 | 7/2010 |
| EP | 2394680 | 12/2011 |
| EP | 1867290 | 2/2013 |
| EP | 2624905 | 8/2013 |
| EP | 2540328 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 3344157 | 4/2018 |
| EP | 2231256 | 5/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 4039205 | 8/2022 |
| EP | 4072613 | 10/2022 |
| EP | 4076611 | 10/2022 |
| EP | 4079239 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| HK | 1162287 | 8/2012 |
| IN | 201837038624 | 10/2020 |
| IN | 202147016649 | 4/2021 |
| JP | 300561 | 10/1992 |
| JP | H6190049 | 7/1994 |
| JP | H07323090 A | 12/1995 |
| JP | 2001522631 | 5/1999 |
| JP | 2000175925 | 6/2000 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |
| JP | 2011526820 | 1/2010 |
| JP | 2011517424 | 6/2011 |
| JP | 2012213478 | 11/2012 |

(56)                    References Cited

FOREIGN PATENT DOCUMENTS

| | | |
|---|---|---|
| JP | 05694718 | 4/2015 |
| JP | 2015208685 | 11/2015 |
| JP | 2016513505 | 5/2016 |
| JP | 2016104212 | 6/2016 |
| JP | 2017533051 | 11/2017 |
| JP | 2018-504988 | 2/2018 |
| JP | 6325543 | 5/2018 |
| JP | 2018525088 | 9/2018 |
| JP | 2022104828 | 7/2022 |
| JP | 2003033359 | 2/2023 |
| JP | 7253376 | 3/2023 |
| JP | 7324264 | 8/2023 |
| JP | 7491974 | 5/2024 |
| KR | 2018045822 | 5/2018 |
| KR | 2020133754 | 11/2020 |
| TW | 7778088 | 9/2022 |
| WO | WO1997017889 | 5/1997 |
| WO | WO1998024501 | 6/1998 |
| WO | WO199833443 | 8/1998 |
| WO | WO199838920 | 9/1998 |
| WO | WO199839053 | 9/1998 |
| WO | WO199851237 | 11/1998 |
| WO | WO1999044542 | 9/1999 |
| WO | WO9951140 | 10/1999 |
| WO | WO2000032118 | 6/2000 |
| WO | WO2000053120 | 9/2000 |
| WO | WO0202162 | 1/2002 |
| WO | WO2002053221 | 7/2002 |
| WO | WO2002055146 | 7/2002 |
| WO | WO2003015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2008039684 | 4/2008 |
| WO | WO2009082513 | 7/2009 |
| WO | WO2009086482 | 7/2009 |
| WO | WO2009105710 | 8/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012114633 | 8/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2014139845 | 9/2014 |
| WO | WO2014207797 | 12/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2016133947 | 8/2016 |
| WO | WO2016186880 | 11/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018100445 | 6/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2020162724 | 8/2020 |
| WO | WO2021020767 | 2/2021 |
| WO | WO2021067134 | 4/2021 |
| WO | WO2021076954 | 4/2021 |
| WO | WO2021127202 | 6/2021 |
| WO | WO2021148490 | 7/2021 |
| WO | WO2021162678 | 8/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2022214020 | 10/2022 |
| WO | WO2022221643 | 10/2022 |
| WO | WO2022223772 | 10/2022 |
| WO | WO2022261448 | 12/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023143700 | 8/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2023239706 | 12/2023 |
| WO | WO2024006482 | 1/2024 |
| WO | WO2024054988 | 3/2024 |
| WO | WO2024059695 | 3/2024 |
| WO | WO2024103036 | 5/2024 |
| WO | WO2024151629 | 7/2024 |
| WO | WO2025014517 | 1/2025 |
| WO | WO2025043128 | 2/2025 |
| WO | WO2025059542 | 3/2025 |
| WO | WO2025106851 | 5/2025 |
| WO | WO2025111572 | 5/2025 |
| WO | WO2025117864 | 6/2025 |
| WO | WO2025188578 | 9/2025 |
| WO | WO2025235015 | 11/2025 |

OTHER PUBLICATIONS

US 12,115,056 B2, 10/2024, Merritt et al. (withdrawn)
International Search Report and Written Opinion for International App. No. PCT/US2023/079428; Applicant: Inari Medical, Inc., Date of Mailing: May 29, 2024, 18 pages.
Extended European Search Report for European Application No. 21818772.2, Applicant: Inari Medical, Inc., Date of Mailing: May 10, 9 pages.
Chinese Office Action received for Application No. 202111061740.2, Applicant: Inari Medical, Inc, Date of Mailing: May 23, 2024, 15 pages.
English translation of Japanese Office Action mailed Jun. 25, 2024 for Japanese Application No. 2022-574456, 5 pages.

(56) References Cited

OTHER PUBLICATIONS

Japanese Office Action mailed Jul. 8, 2024 for Japanese Application No. 2022-522892, 14 pages.
Chinese first Office Action mailed May 10, 2024 for Chinese Application No. 202080087833.X, 11 pages.
Partial Supplementary European Search Report received for European Application No. 21852966.7; Applicant: Inari Medical, Inc., Date of Mailing: Jul. 23, 2024, 12 pages.
Japanese Office Action mailed Aug. 2, 2024 for Japanese Application No. 2023-213724, 3 pages.
English Translation of Japanese Office Action mailed Jul. 23, 2024 for Japanese Application No. 2022-535535, 11 pages.
Extended European Search Report received for European Application No. 21895504.5; Applicant: Inari Medical, Inc., Date of Mailing: Aug. 16, 2024, 10 pages.
English translation of Japanese Office Action mailed Sep. 17, 2024 for Japanese Application No. 2023-203650, 6 pages.
English machine translation of Japanese Office Action mailed Oct. 10, 2024 for Japanese Application No. 2022-522892, 11 pages.
International Search Report and Written Opinion for International App. No. PCT/US2024/043504; Applicant: Inari Medical, Inc., Date of Mailing: Nov. 12, 2024, 12 pages.
International Search Report and Written Opinion for International App. No. PCT/US2024/037570; Applicant: Inari Medical, Inc., Date of Mailing: Nov. 20, 2024, 12 pages.
International Search Report and Written Opinion for International App. No. PCT/US2024/046723; Applicant: Inari Medical, Inc., Date of Mailing: Nov. 27, 2024, 11 pages.
English translation of Chinese Office Action mailed Jan. 22, 2025 for Chinese Application No. 202210842779.6, 17 pages.
Extended European Search Report received for European Application No. 24209030.6; Applicant: Inari Medical, Inc., Date of Mailing: Feb. 3, 2025, 7 pages.
International Search Report and Written Opinion for International App. No. PCT/US2024/056178; Applicant: Inari Medical, Inc., Date of Mailing: Mar. 24, 2025, 13 pages.
International Search Report and Written Opinion for International App. No. PCT/US2024/057919; Applicant: Inari Medical, Inc., Date of Mailing: Mar. 28, 2025, 13 pages.
English translation of Chinese Second Office Action mailed Apr. 24, 2025 for Chinese Application No. 202080097026.6, 10 pages.
International Search Report for International Application No. PCT/US2023/026648, mailed on Dec. 19, 2023, 6 pages.
Written Opinion of the International Searching Authority for International Application No. PCT/US2023/026648, dated Dec. 19, 2023, 31 pages.
Bayer HealthCare, 'Our Next Generation Aspiration Catheter.' Fetch 2 Catheter Specifications, Feb. 2013, 2 pages.
Medtronic, Solitaire X, Revascularization Device. http://www.ev3.net/neuro/intl/remodeling-devices/solitaire-ab.htm. 6 pages, (2019).
International Search Report and Written Opinion for International App. No. PCT/US2023/074169; Applicant: Inari Medical, Inc., Date of Mailing: May 1, 2024, 12 pages.
English translation of Japanese Office Action for Japanese Application No. 2023-507628 mailed Apr. 23, 2025, 8 pages.
Gross et al., "Dump the pump: manual aspiration thrombectomy (MAT) with a syringe is technically effective, expeditious, and cost-efficient," J NeuroIntervent Surg, 2018, 4 pages.
International Search Report and Written Opinion for International App. No. PCT/US23/60927; Date of Filing: Jan. 19, 2023, Applicant: Inari Medical, Inc., Date of Mailing: Jul. 20, 2023, 12 pages.
Extended European Search Report issued for EP Application No. 20877370.5, Date of Mailing: Oct. 17, 2023, 11 pages.
International Search Report and Written Opinion for International App. No. PCT/US23/65128; Date of Filing: Mar. 30, 2023, Applicant: Inari Medical, Inc., Date of Mailing: Nov. 14, 2023, 14 pages.
International Search Report and Written Opinion for International App. No. PCT/US23/66538; Date of Filing: May 3, 2023, Applicant: Inari Medical, Inc., Date of Mailing: Jan. 4, 2024, 14 pages.

English translation of Japanese Office Action received for JP Application No. 2022-574456, Applicant: Inari Medical, Inc, Date of Mailing: Jan. 23, 2024, 12 pages.
Chinese First Office Action received for CN Application No. 201980067623.1, Applicant: Inari Medical, Inc., Date of Mailing: Jan. 31, 2024, 10 pages.
International Search Report and Written Opinion for International App. No. PCT/US23/73765; Date of Filing: Sep. 8, 2023, Applicant: Inari Medical, Inc., Date of Mailing: Feb. 28, 2024, 7 pages.
International Search Report and Written Opinion for International App. No. PCT/US23/69892; Date of Filing: Jul. 10, 2023, Applicant: Inari Medical, Inc., Date of Mailing: Feb. 29, 2024, 12 pages.
English translation of Japanese Office Action mailed Jan. 19, 2024 for Japanese Application No. 2022-160947, 8 pages.
International Search Report and Written Opinion for International App. No. PCT/US2024/010875; Applicant: Inari Medical, Inc., Date of Mailing: Apr. 26, 2024, 15 pages.
Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.
Gupta, S. et al., "Acute Pulmonary Embolism Advances in Treatment", JAPI, Association of Physicians India, Mar. 2008, vol. 56, 185-191.
International Search Report and Written Opinion for International App. No. PCT/US13/61470, mailed Jan. 17, 2014, 7 pages.
International Search Report and Written Opinion for International App. No. PCT/US2014/046567, mailed Nov. 3, 2014, 13 pages.
International Search Report and Written Opinion for International App. No. PCT/US2014/061645, mailed Jan. 23, 2015, 15 pages.
International Search Report for International App. No. PCT/US13/71101, mailed Mar. 31, 2014, 4 pages.
Konstantinides, S. et al., "Pulmonary embolism hotline 2012—Recent and expected trials", Thrombosis and Haemostasis, Jan. 9, 2013:33; 43-50.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: In Vitro and in Vivo Testing", Circulation, Sep. 2005:112:e28-e32.
Kucher, N., "Catheter Interventions in Massive Pulmonary Embolism", Cardiology Rounds, Mar. 2006 vol. 10, Issue 3, 6 pages.
Kucher, N. et al., "Management of Massive Pulmonary Embolism", Radiology, Sep. 2005:236:3 852-858.
Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.
Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al., "Massive pulmonary embolism: review of management strategies with a focus on catheter-based techniques", Expert Rev. Cardiovasc. Ther. 8(6), 863-873 (2010).
Liu, S. et al., "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Reekers, J. et al., "Mechanical Thrombectomy for Early Treatment of Massive Pulmonary Embolism", CardioVascular and Interventional Radiology, 2003: 26:246-250.

(56)                    References Cited

OTHER PUBLICATIONS

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol27-254-258, 2004, 5 pgs.

Turk et al., "ADAPT FAST study: a direct aspiration first pass technique for acute stroke thrombectomy." J NeuroIntervent Surg, vol. 6, 2014, 6 pages.

Uflacker, R., "Interventional Therapy for Pulmonary Embolism", Journal of Vascular and Interventional Radiology, Feb. 2001: 12:147-164.

Verma, R., MD et al. "Evaluation of a Newly Developed Percutaneous Thrombectomy Basket Device in Sheep With Central Pulmonary Embolisms", Investigative Radiology, Oct. 2006, 41, 729-734.

International Search Report and Written Opinion for International App. No. PCT/US2015/034987 filed Jun. 9, 2015, Applicant: Inceptus Medical, LLC, Date of Mailing: Sep. 17, 2015, 12 pages.

International Search Report and Written Opinion for International App. No. PCT/US2016/067628 filed Dec. 19, 2016, Applicant: Inari Medical, Inc., Date of Mailing: Apr. 10, 2017, 11 pages.

Goldhaber, S. et al. "Percutaneous Mechanical Thrombectomy for Acute Pulmonary Embolism—A Double-Edged Sword," American College of CHEST Physicians, Aug. 2007, 132:2, 363-372.

Goldhaber, S., "Advanced treatment strategies for acute pulmonary embolism, including thrombolysis and embolectomy," Journal of Thrombosis and Haemostasis, 2009: 7 (Suppl. 1): 322-327.

International Search Report and Written Opinion for International App. No. PCT/US2017/029696, Date of Filing: Apr. 26, 2017, Applicant: Inari Medical, Inc., Date of Mailing: Sep. 15, 2017, 19 pages.

International Search Report and Written Opinion for International App. No. PCT/US2016/058536, Date of Filing: Oct. 24, 2016, Applicant: Inari Medical, Inc., Date of Mailing: Mar. 13, 2017, 14 pages.

International Search Report and Written Opinion for International App. No. PCT/US2018/048786, Date of Filing: Aug. 30, 2018, Applicant: Inari Medical, Inc., Date of Mailing: Dec. 13, 2018, 12 pages.

International Search Report and Written Opinion for International App. No. PCT/US2018/055780, Date of Filing: Oct. 13, 2018, Applicant: Inceptus Medical LLC., Date of Mailing: Jan. 22, 2019, 8 pages.

International Search Report and Written Opinion for International App. No. PCT/US2019/045794, Date of Filing: Aug. 8, 2019, Applicant: Inari Medical, Inc., Date of Mailing: Nov. 1, 2019, 17 pages.

International Search Report and Written Opinion for International App. No. PCT/US2020/056067, Date of Filing: Oct. 16, 2020; Applicant: Inari Medical, Inc., Date of Mailing: Jan. 22, 2021, 8 pages.

International Search Report and Written Opinion for International App. No. PCT/US2020/055645, Date of Filing: Dec. 17, 2020; Applicant: Inari Medical, Inc., Date of Mailing: Apr. 14, 2021, 12 pages.

Vorwerk, D. MD, et al., "Use of a Temporary Caval Filter to Assist Percutaneous Iliocaval Thrombectomy: Experimental Results." SCVIR, 1995, 4 pages.

Wikipedia; Embolectomy; retrieved from the internet: https://en.wikipedia.org/wiki/Embolectomy; 4 pgs.; retrieved/printed: Mar. 24, 2016.

O'Sullivan; Thrombolysis versus thrombectomy in acute deep vein thrombosis; Interventional Cardiology; 3(5); pp. 589-596; Oct. 2011.

Capture Vascular Systems; (company website); retrieved from the internet: http://www.capturevascular.com; 3 pgs.; retrieved/printed: Mar. 24, 2016.

Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.

Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.

Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.

Youtube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.

Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.

International Search Report and Written Opinion for International App. No. PCT/US21/35965, Date of Filing: Jun. 4, 2021, Applicant: Inari Medical, Inc., Date of Mailing: Sep. 28, 2021, 12 pages.

International Search Report and Written Opinion for International App. No. PCT/US21/45072 Date of Filing: Aug. 6, 2021, Applicant: Inari Medical, Inc., Date of Mailing: Jan. 20, 2022, 10 pages.

International Search Report and Written Opinion for International App. No. PCT/US21/58793; Date of Filing: Nov. 10, 2021, Applicant: Inari Medical, Inc., Date of Mailing: Mar. 16, 2022, 13 pages.

International Search Report and Written Opinion for International App. No. PCT/US21/59718; Date of Filing: Nov. 17, 2021, Applicant: Inari Medical, Inc., Date of Mailing: Mar. 22, 2022, 13 pages.

International Search Report and Written Opinion for International App. No. PCT/US21/59735; Date of Filing: Nov. 17, 2021, Applicant: Inari Medical, Inc., Date of Mailing: Mar. 22, 2022, 11 pages.

International Search Report and Written Opinion for International App. No. PCT/US23/60502; Date of Filing: Jan. 11, 2023, Applicant: Inari Medical, Inc., Date of Mailing: May 25, 2023, 9 pages.

International Search Report and Written Opinion for International App. No. PCT/US23/61256; Date of Filing: Jan. 25, 2023, Applicant: Inari Medical, Inc., Date of Mailing: Jun. 7, 2023, 8 pages.

English translation of Japanese Office Action for Japanese Application No. 2023-507628 mailed Oct. 28, 2025, 10 pages.

Extended European Search Report received for European Application No. 23740802.6; Applicant: Inari Medical, Inc., Date of Mailing: Nov. 3, 2025, 10 pages.

* cited by examiner

CLOT TREATMENT SYSTEMS WITH DILATOR LOCKING MECHANISMS, AND ASSOCIATED DEVICES AND METHODS

CROSS-REFERENCE TO RELATED APPLICATION

This application claims the benefit of U.S. Provisional Patent Application No. 63/307,766 filed Feb. 8, 2022, and titled "CLOT TREATMENT SYSTEMS WITH DILATOR LOCKING MECHANISMS, AND ASSOCIATED DEVICES AND METHODS," which is incorporated herein by reference in its entirety.

TECHNICAL FIELD

The present technology generally relates to vascular access systems, such as clot treatment systems, including locking mechanisms for releasably locking a dilator to a catheter to facilitate their joint navigation through a patient's skin, tissue, and vasculature.

BACKGROUND

Thrombosis is the local coagulation or clotting of the blood in a part of the circulatory system, and a thrombus is a blood clot formed in situ within the vascular system. A venous thrombus is a blood clot that forms within a vein. A common type of venous thrombosis is a deep vein thrombosis (DVT), which is the formation of a blood clot within a deep vein (e.g., predominantly in the legs). Nonspecific signs of a thrombosis may include pain, swelling, redness, warmness, and engorged superficial veins.

If the thrombus breaks off (embolizes) and flows towards the lungs, it can become a life-threatening pulmonary embolism (PE) (e.g., a blood clot in the lungs). In addition to the loss of life that can arise from PE, DVT can cause significant health issues such as post thrombotic syndrome, which can cause chronic swelling, pressure, pain, and ulcers due to valve and vessel damage. Further, DVT can result in significant health-care costs either directly or indirectly through the treatment of related complications and inability of patients to work.

Existing methods for treating DVT and PE often involve treating the DVT or PE with a catheter system that is advanced through the patient's vasculature, such as along a venous access path. Such catheter systems—especially those having a large size (e.g., greater than 16 French)—often include a dilator component that is inserted through a catheter and used to dilate the vasculature while the catheter is navigated to a target treatment site. Similarly, such systems are often used in conjunction with an introducer sheath that acts as a resealable access point through which the DVT and PE catheter systems can traverse to easily access the vasculature. The introducer sheath provides a stable tract and prevents excessive manipulation of devices with the access site, and can be inserted through the skin and tissue tract with a dilator component interested therein.

However, during advancement of a catheter through the vasculature, the dilator component and/or the catheter can experience considerable force or resistance from the patient's vasculature. Similarly, during insertion of an introducer sheath, the dilator component and/or the introducer sheath can experience considerable force or resistance from the patient's skin and tissue. In some instances, the force against the dilator component can cause the dilator component to retract or backslide within the catheter/introducer sheath. If the dilator retracts far enough, the edge of the catheter/introducer sheath can be exposed and may cause damage to a percutaneous access site or the vasculature of the patient.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Figure 1:
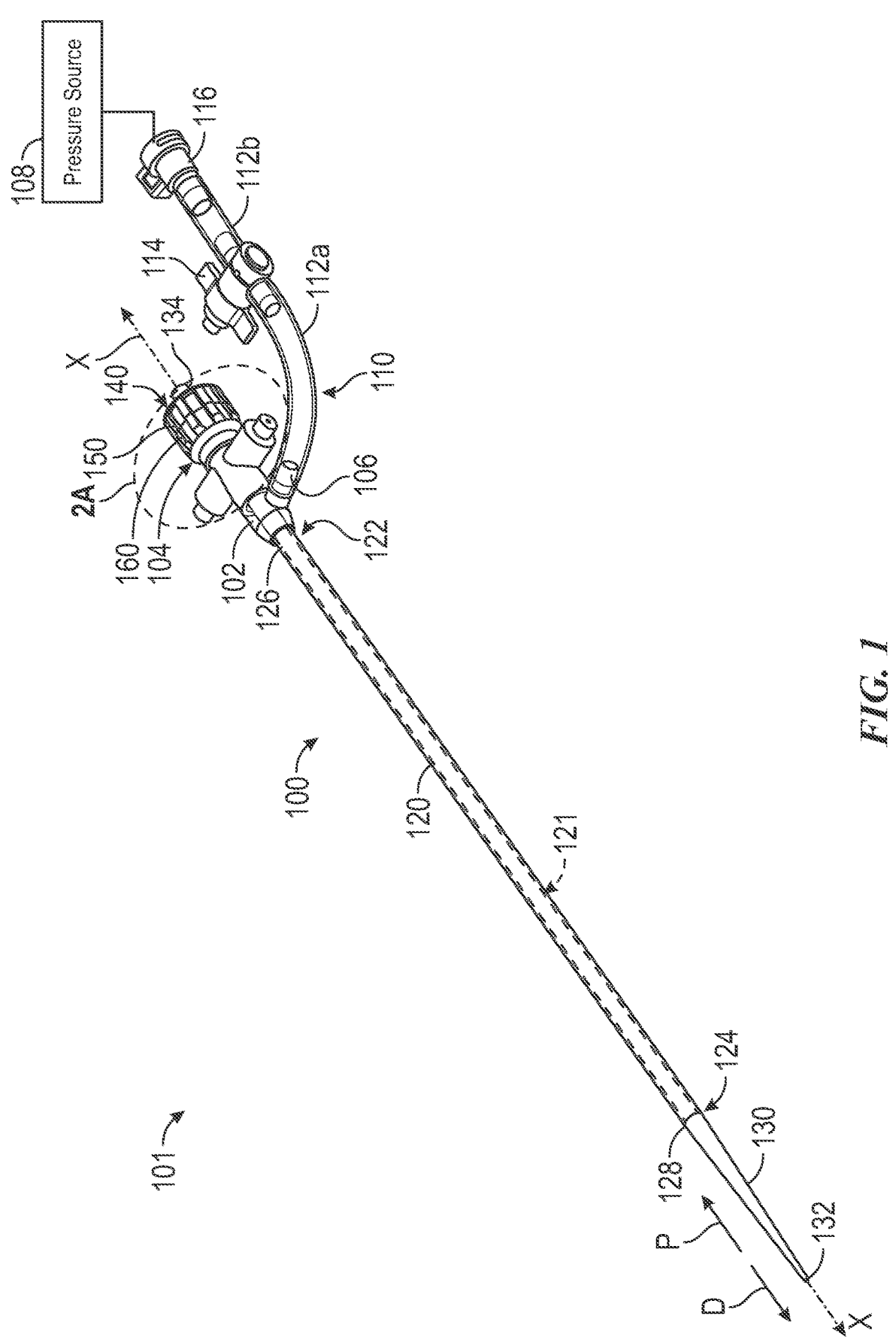
FIG. 1 is a partially schematic side view of a vascular access system including a cap assembly and configured in accordance with the present technology.

The present technology is generally directed to vascular access systems with dilator locking mechanisms, and associated devices and methods. In some of the embodiments described in detail below, a dilator locking mechanism includes a first cap coupled to a dilator and a second cap coupled to a catheter (e.g., an aspiration catheter, an introducer/access sheath) of, for example, a clot treatment system. The first cap can include one or more locking members, and the second cap can include one or more locking features corresponding to one or more of the locking members. Each of the locking members (first cap) can be aligned with and inserted at least partially into the corresponding locking feature (second cap) to, for example, couple the first cap to the second cap. Because the first cap is coupled to the dilator, the interaction between the first and second caps when coupled can secure the dilator relative to the catheter to inhibit or even prevent the dilator from moving proximally and/or distally relative to the catheter.

In some embodiments, the locking features are configured to deflect the locking members into a locked position when the locking members are inserted therein. In these and other embodiments, the first cap can be rotated relative to the second cap (and/or the second cap rotated relative to the first cap) to move the locking members from the locked position to an unlocked position to uncouple the dilator locking mechanism and allow the dilator to move relative to the catheter of the vascular access system.

Current dilator locking mechanisms may involve a direct connection between the associated dilator and vascular access system. For example, such locking mechanisms may require that the dilator be fully advanced through the clot treatment system and then rotated to secure the dilator. With this style of mechanism, it may be difficult for an operator to distinguish (e.g., visually) between situations where the dilator is (i) fully inserted into and secured to the clot treatment system and (ii) fully inserted into but not secured to the clot treatment system. In contrast to these current mechanisms, the dilator locking mechanisms of the present technology can be located at or near a proximal end of the clot treatment system, such that a user of the clot treatment system (e.g., a physician) can easily observe the first and second caps to determine whether the dilator is secured to the clot treatment system by observing the relative positions and/or alignment of the first and second caps.

Certain details are set forth in the following description and in FIGS. 1-8 to provide a thorough understanding of various embodiments of the present technology. In other instances, well-known structures, materials, operations, and/or systems often associated with intravascular procedures, clot removal procedures, catheters, and the like are not shown or described in detail in the following disclosure to avoid unnecessarily obscuring the description of the various embodiments of the technology. Those of ordinary skill in the art will recognize, however, that the present technology can be practiced without one or more of the details set forth herein, and/or with other structures, methods, components, and so forth.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope unless expressly indicated. The sizes of various depicted elements are not necessarily drawn to scale, and these various elements may be enlarged to improve legibility. Component details may be abstracted in the Figures to exclude details such as position of components and certain precise connections between such components when such details are unnecessary for a complete understanding of how to make and use the present technology. Many of the details, dimensions, angles and other features shown in the Figures are merely illustrative of particular embodiments of the disclosure. Accordingly, other embodiments can have other details, dimensions, angles and features without departing from the present technology. In addition, those of ordinary skill in the art will appreciate that further embodiments of the present technology can be practiced without several of the details described below.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," and the like are not meant to limit the referenced component to a specific orientation. It will be appreciated that such designations refer to the orientation of the referenced component as illustrated in the Figures; the systems of the present technology can be used in any orientation suitable to the user.

FIG. 1 is a partially schematic side view of a vascular access system 100 ("the system 100") configured in accordance with embodiments of the present technology. The system 100 can also be referred to as an aspiration assembly, a clot treatment system, a clot removal system, a thrombectomy system, an introducer sheath assembly, and/or the like. In the illustrated embodiment, the system 100 includes a tubing assembly 110 fluidly coupled to a catheter 120 via a valve 102. In some embodiments, the catheter 120 is an elongate member configured to be inserted into and through a patient's vasculature and used to, for example, treat clot material therein. In other embodiments, the catheter 120 can be an introducer sheath configured to be inserted through the skin and tissue tract of the patient to provide an access site through which other components (e.g., other catheters used to treat clot material) can traverse to easily access the vasculature. Accordingly, while referred to as "catheter 120," the catheter 120 can comprise an introducer sheath, an access sheath, and/or another type of elongate member configured to be inserted through the skin and tissue tract and/or to traverse the vasculature of a patient. In general, the system 100 (i) can include features generally similar or identical to those of the clot treatment systems described in detail in U.S. patent application Ser. No. 16/536,185, filed Aug. 8, 2019, and titled "SYSTEM FOR TREATING EMBOLISM AND ASSOCIATED DEVICES AND METHODS," which is incorporated herein by reference in its entirety, and/or (ii) can be used to treat/remove clot material from a patient (e.g., a human patient) using any of the methods described in detail therein.

In the illustrated embodiment, the catheter 120 includes a proximal region or portion 122 and a distal tip region or portion 124 opposite the proximal region 122. The catheter 120 further defines a lumen 121 (shown in dashed-line in FIG. 1) extending entirely therethrough from the proximal region 122 to the distal tip region 124. The lumen 121 and/or the catheter 120 can at least partially define a longitudinal axis X of the system 100. The proximal region 122 can include a proximal terminus 126 of the catheter 120, and the distal tip region 124 can include a distal terminus 128 of the catheter 120.

The valve 102 is fluidly coupled to the lumen 121 of the catheter 120 and can be integral with or coupled to the proximal region 122 of the catheter 120 such that these components move together. In some embodiments, the valve 102 is a hemostasis valve that is configured to maintain hemostasis during a clot removal procedure by preventing fluid flow in a proximal direction P through the valve 102 as various components such as dilators, delivery sheaths, pull members, guidewires, interventional devices, other aspiration catheters, and so on are inserted through the valve 102 to be delivered through the catheter 120 to a treatment site in a blood vessel. In the illustrated embodiment, for example, a dilator 130 is inserted through the valve 102 and positioned within the catheter 120. The valve 102 includes a branch or side port 106 configured to fluidly couple the lumen 121 of the catheter 120 to the tubing assembly 110. In some embodiments, the valve 102 can be a valve of the type disclosed in U.S. patent application Ser. No. 16/117, 519, filed Aug. 30, 2018, and titled "HEMOSTASIS VALVES AND METHODS OF USE," which is incorporated herein by reference in its entirety.

In the illustrated embodiment, the tubing assembly 110 fluidly couples the catheter 120 to a pressure source 108, such as a syringe. The pressure source 108 can be configured to generate (e.g., form, create, charge, build-up) a vacuum (e.g., negative relative pressure) and store the vacuum for subsequent application to the catheter 120 (e.g., after the dilator 130 has been removed from the catheter 120). The tubing assembly 110 can include one or more tubing sections 112 (individually labeled as a first tubing section 112*a* and a second tubing section 112*b*), at least one fluid control device 114 (e.g., a valve), and at least one connector 116 (e.g., a Toomey tip connector) for fluidly coupling the tubing assembly 110 to the pressure source 108 and/or other suitable components. In some embodiments, the fluid control device 114 is a stopcock that is fluidly coupled to (i) the side port 106 of the valve 102 via the first tubing section 112*a* and (ii) the connector 116 via the second tubing section 112*b*. The fluid control device 114 is externally operable by a user to regulate the flow of fluid therethrough and, specifically, from the lumen 121 of the catheter 120 to the pressure source 108. In some embodiments, the connector 116 is a quick-release connector (e.g., a quick disconnect fitting) that enables rapid coupling/decoupling of the catheter 120 and the fluid control device 114 to/from the pressure source 108.

In the illustrated embodiment, the dilator 130 is inserted through the valve 102 in a distal direction D and extends fully through the lumen 121 and past the distal terminus 128 of the catheter 120, such that a distal tip 132 (e.g., an atraumatic tip) of the dilator 130 is positioned beyond the distal terminus 128 of the catheter 120. The dilator 130 and the system 100 can together define a catheter or introducer assembly 101 that can be inserted into a patient (e.g., a human patient) during a clot treatment procedure. For example, the dilator 130 and the system 100 can be inserted into and advanced together through a blood vessel of the patient to a target location in the blood vessel. The dilator 130 can then be retracted proximally (e.g., in the proximal direction P) through the system 100 to allow for other intravascular medical devices to be introduced into the patient via the system 100 and/or for aspiration of the catheter 120. For example, in some embodiments the system 100 and/or the catheter assembly 101 can be used in any of the clot removal procedures disclosed in U.S. patent application Ser. No. 16/536,185, filed Aug. 8, 2019, and titled "SYSTEM FOR TREATING EMBOLISM AND ASSOCIATED DEVICES AND METHODS," which is incorporated herein by reference in its entirety.

The catheter assembly 101 can include a locking mechanism or cap assembly 140 (which can also be referred to as a locking cap assembly, a dilator locking mechanism, a dilator coupling mechanism, and/or the like) configured to releasably couple and secure the dilator 130 to the system 100. The cap assembly 140 can lock the dilator 130 to the valve 102 and the catheter 120 to inhibit or even prevent the dilator 130 from moving within the catheter 120 in the proximal direction P and/or the distal direction D when the catheter assembly 101 is advanced through the vasculature of a patient. More specifically, for example, the cap assembly 140 can inhibit or even prevent the distal tip 132 of the dilator 130 from moving proximally toward the distal terminus 128 of the catheter 120 when the catheter assembly 101 is advanced through the vasculature of the patient.

In the illustrated embodiment, the cap assembly 140 includes (i) a first or proximal cap 150 coupled to or integrally formed with the dilator 130 (via, e.g., a coupling element or luer connector 134) opposite the distal tip 132 and (ii) a second or distal cap 160 coupled to a proximal portion 104 of the valve 102. The first cap 150 can be releasably coupled/locked to the second cap 160. Accordingly, inserting the dilator 130 into the catheter 120 can include moving the first cap 150 toward the second cap 160.

In some embodiments, the first cap 150 can mate with the second cap 160 to lock the dilator 130 to the valve 102 when the dilator 130 is fully seated within the system 100. In some aspects of the present technology, a user can easily determine the state of the dilator 130 (e.g., how far the dilator 130 is inserted into the catheter 120 and/or whether the dilator 130 is secured to the system 100) by viewing the cap assembly 140. Additional details regarding the cap assemblies of the present technology, including the cap assembly 140, are discussed in detail below with reference to FIGS. 2A-8.

During a clot treatment procedure, the catheter assembly 101 can be inserted through the vasculature of a patient (e.g., through an introducer sheath that traverses the skin and tissue of the patient to provide an access site) with the cap assembly 140 locking the dilator 130 to the valve 102 and the catheter 120. When the catheter 120 is positioned at a desired position relative to clot material (e.g., a pulmonary embolism, deep vein thrombosis) within the patient, the cap assembly 140 can be unlocked and the dilator 130 withdrawn from the catheter 120. Then, a user can first close the fluid control device 114 before generating a vacuum in the pressure source 108 by, for example, withdrawing the plunger of a syringe coupled to the connector 116. In this manner, a vacuum is charged within the pressure source 108 (e.g., a negative pressure is maintained) before the pressure source 108 is fluidly connected to the lumen 121 of the catheter 120. To aspirate the lumen 121 of the catheter 120, the user can open the fluid control device 114 to fluidly connect the pressure source 108 to the catheter 120 and thereby apply or release the vacuum stored in the pressure source 108 to the lumen 121 of the catheter 120. Opening of the fluid control device 114 instantaneously or nearly instantaneously applies the stored vacuum pressure to the tubing assembly 110 and the catheter 120, thereby generating a suction pulse throughout the catheter 120 that can aspirate the clot material into the catheter 120. In particular, the suction is applied at the distal tip region 124 of the catheter 120 to suck/aspirate at least a portion of the clot material proximate the distal tip region 124 into the lumen 121 of the catheter 120. In other embodiments, where the catheter 120 is an introducer sheath, the introducer assembly 101 can be inserted through the skin and tissue of a patient and partially into a vessel to provide an access point for other medical instruments.

Figure 2A:
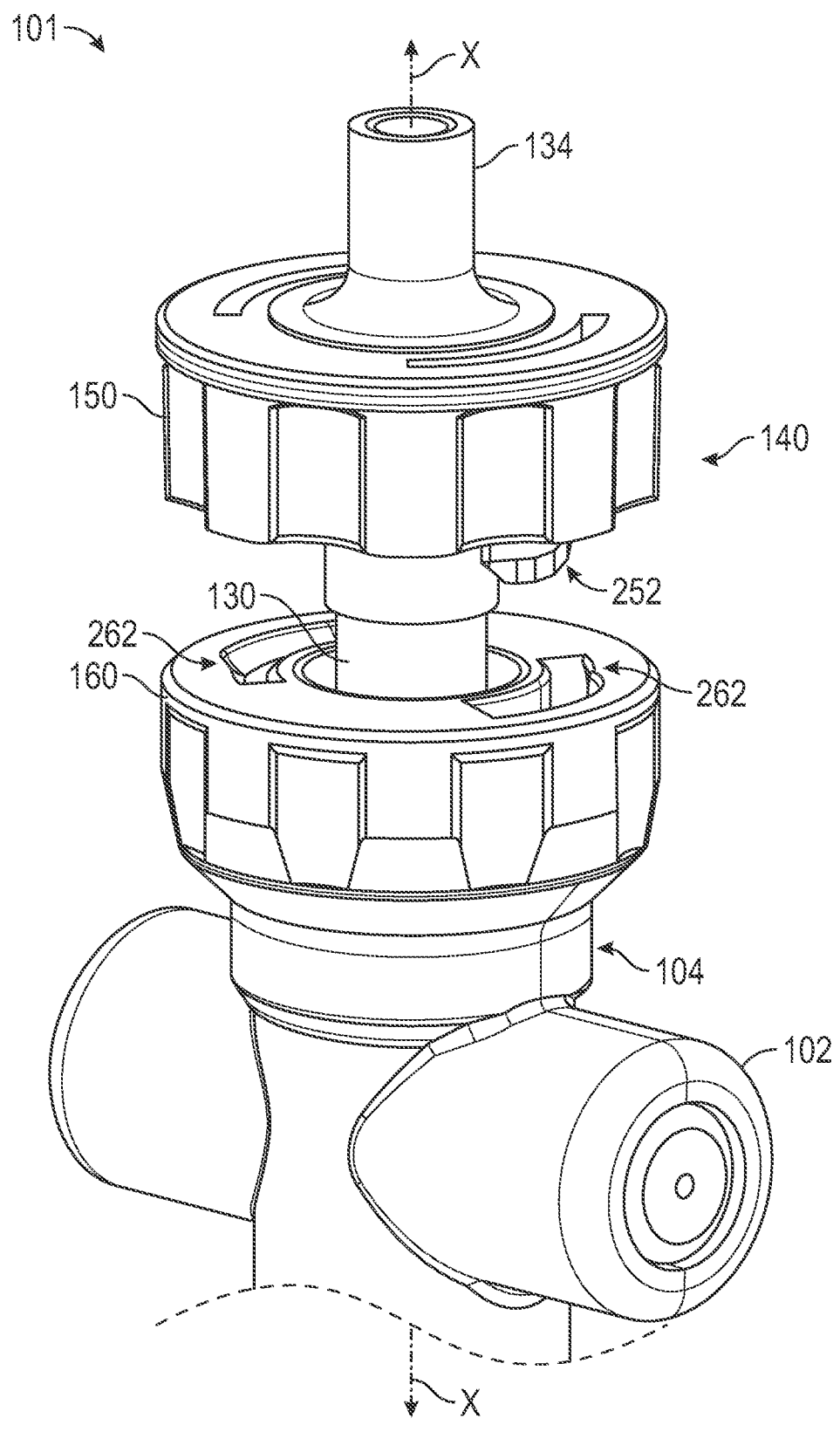
FIG. 2A-2C are a partially-exploded isometric view, a side cross-sectional view, and an enlarged view, respectively, of the cap assembly of FIG. 1 in accordance with embodiments of the present technology.

FIG. 2A is a partially-exploded isometric view of cap assembly 140 of FIG. 1 in accordance with embodiments of the present technology. In the illustrated embodiment, the cap assembly 140 is in an unlocked position in which the first cap 150 is not secured to the second cap 160 such that the dilator 130 is free to move relative to the valve 102 and the catheter 120 (FIG. 1). The first cap 150 can include one or more coupling or locking members 252 extending (e.g., downwardly, distally, and/or toward the second cap 160) in a direction parallel or generally parallel to the longitudinal axis X. In the illustrated embodiment, the first cap 150 includes two of the locking members 252 (one of the locking members 252 is obscured in FIG. 2A) positioned on opposite sides of the first cap 150 (e.g., 180-degrees apart). The second cap 160 can include one or more coupling or locking features 262 that extend through the second cap 160 at least partially about the longitudinal axis X. In the illustrated embodiment, the locking members 252 are projections and the locking features 262 are corresponding grooves or openings. In other embodiments, the first cap 150 can include more or fewer of the locking members 252 and/or the second cap 160 can include more or fewer of the locking features 262. For example, the first cap 150 can include one or more than two of the locking members 252, and the second cap 160 can include the same number of the locking features 262. In the illustrated embodiment, the first cap 150 and the second cap 160 have circular shapes. In other embodiments, the first cap 150 and/or the second cap 160 can have a triangular, square, rectangular, rectilinear, curvilinear, or any other suitable shape. In at least some embodiments, the first cap 150 and the second cap 160 can have a same shape. In other embodiments, the first cap and the second cap can have different shapes.

Each of the locking members 252 can be relatively flexible and configured to undergo elastic or generally elastic deformations. Additionally, each of the locking features 262 can be configured (e.g., shaped and sized) to bend or deflect the corresponding locking members 252 inwardly (toward the longitudinal axis X) to facilitate locking/coupling of the first cap 150 to the second cap 160. In the illustrated embodiment, individual ones of the locking features 262 are configured (e.g., shaped, sized, positioned) to releasably receive a corresponding one of the locking members 252. In general, to secure (e.g., couple, lock) the first cap 150 to the second cap 160, the locking members 252 can be at least partially aligned with and inserted into the corresponding locking features 262. Once inserted, the outward bias of the locking members 252 can cause the locking members 252 to engage the corresponding locking features 262 (and/or another portion of the valve 102) to secure the first cap 150 to the second cap 160. In some embodiments, aligning the locking members 252 with the corresponding locking features 262 can include rotating the first cap 150 (e.g., about the longitudinal axis X) relative to the second cap 160.

In operation, inserting the dilator 130 into the valve 102 and the catheter 120 includes moving the first cap 150 toward the second cap 160. While moving the dilator 130 through the valve 102, the user can rotate the first cap 150 such that individual ones of the locking members 252 are at least partially aligned with the corresponding ones of the locking features 262. With the locking members 252 and the corresponding locking features 262 in this orientation, the user can bring the first cap 150 into contact with the second cap 160 to insert the locking members 252 into the corresponding locking features 262 and secure the first cap 150 to the second cap 160.

Figure 2B:
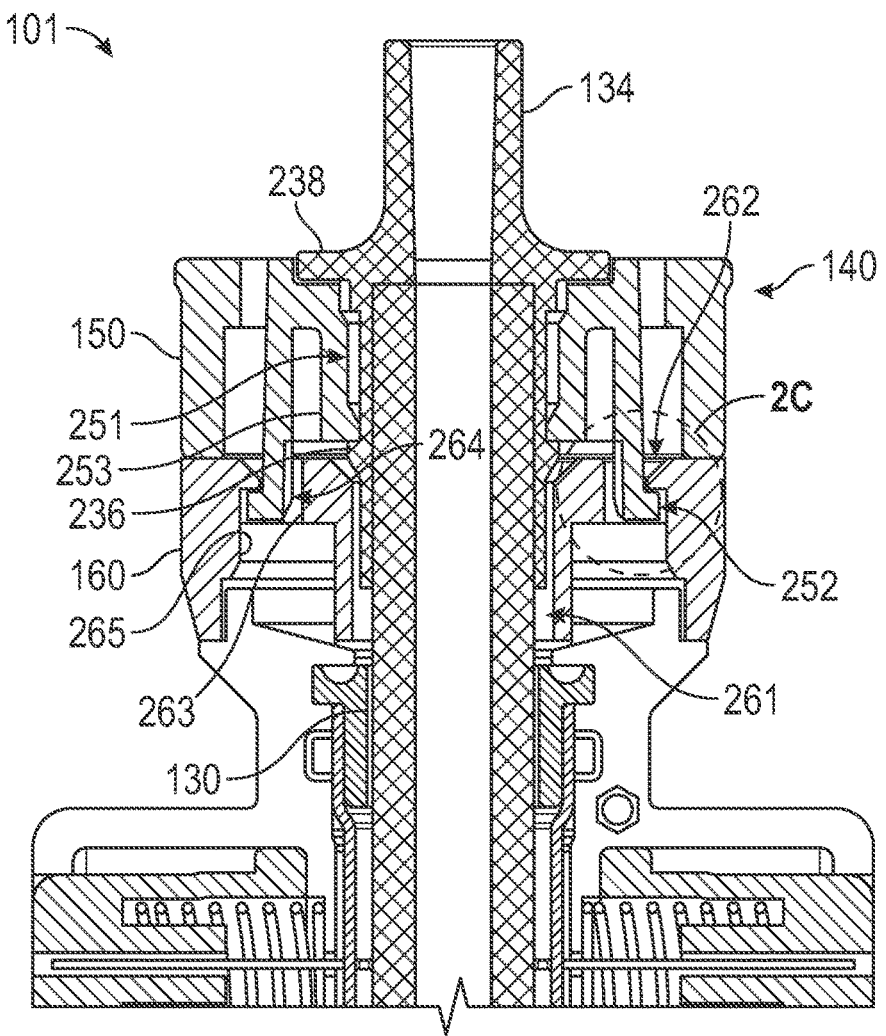
Figure 2C:
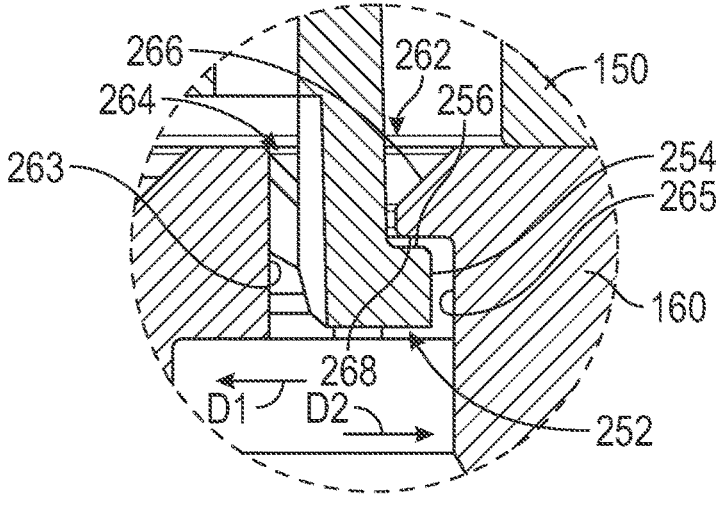

More specifically, FIG. 2B is a side cross-sectional view of the cap assembly 140 of FIG. 2A in accordance with embodiments of the present technology. FIG. 2C is an enlarged view of a region 2C of FIG. 2B in accordance with embodiments of the present technology. The cap assembly 140 is in a locked position in FIGS. 2B and 2C in which the first cap 150 is secured to the second cap 160 such that the dilator 130 is locked in position relative to the valve 102 and the catheter 120 (FIG. 1). Referring to FIGS. 2B and 2C together, each of the locking features 262 of the second cap 160 can include a channel or slot 264 defined at least partially by a first or inner wall 263 and a second or outer wall 265 spaced radially apart from the inner wall 263. In the locked position shown in FIGS. 2B and 2C, the locking members 252 are inserted into the corresponding locking features 262 such that at least a portion of the locking members 252 are positioned in the slots 264 of the corresponding locking features 262 between the inner wall 263 and the outer wall 265.

Referring to FIG. 2B, in some embodiments the second cap 160 includes an opening 261 sized, positioned, and/or otherwise configured to allow the dilator 130 to pass through the second cap 160. The first cap 150 is secured to the dilator 130 and can include an opening 251 configured to receive the dilator 130 and a connected or integral luer connector 134. In the illustrated embodiment, for example, the opening 251 is at least partially defined by one or more luer coupling members 253. Each of the luer coupling members 253 can be positioned radially inward relative to one or more of the locking members 252. Additionally, each of the luer coupling members 253 can be generally flexible and configured to undergo elastic or generally elastic deformations. The luer connector 134 can include a first or distal flange 236 and a second or proximal flange 238 opposite and spaced apart from the distal flange 236. The dilator 130 and the luer connector 134 can be inserted through the opening 251 such that the distal flange 236 contacts individual ones of the luer coupling members 253 to cause the luer coupling members 253 to bend or deflect radially outward away from the luer connector 134. Once the distal flange 236 has moved distally past the luer coupling members 253, the luer coupling members 253 can return to their original (e.g., unbent) configuration, as shown in FIG. 2B. With the luer connector 134 and the luer coupling members 253 in the respective positions shown in FIG. 2B, at least a portion of the first cap 150 (e.g., the luer coupling members 253) can be positioned between the distal flange 236 and the proximal flange 238 to secure the dilator 130 to the first cap 150. In other embodiments, the dilator 130 can be secured to the first cap 150 in other manners.

Referring to FIG. 2C, each of the locking features 262 in the second cap 160 can further include a first surface 266 (which can also be referred to as a proximal, deflecting, angled, and/or insertion surface) and a second surface 268 (which can also be referred to as a distal, retaining, and/or locking surface). The second surface 268 can extend from the outer wall 265 toward the inner wall 263 in an inward direction perpendicular or generally perpendicular to the inner and/or outer walls 263, 265. The first surface 266 can extend upwardly at an incline from the second surface 268 and away from the inner wall 263, to, for example, form an acute interior angle with the second surface 268. In other embodiments, the first and second surfaces 266, 268 can be positioned on the inner wall 263 opposite the outer wall 265, or have any other suitable configuration.

Each of the locking members 252 can include a tab 254. Each tab 254 can be positioned at or near a distal end of the associated locking members 252. In the illustrated embodiment, the tab 254 extends outward and/or perpendicularly from the associated locking member 252 (e.g., toward the outer wall 265). In other embodiments, one or more of the tabs 254 can extend inward from the associated locking member 252 (e.g., toward the inner wall 263), or in any other suitable direction. The tab 254 can define a stopping or retaining surface 256. When the first cap 150 is coupled to the second cap 160, as shown in FIG. 2C, the retaining surface 256 is at least partially aligned with and/or parallel to the second surface 268. The alignment of the retaining surface 256 with the second surface 268 can prevent, or at least partially prevent, the first cap 150 from moving (e.g., upwardly and/or proximally) relative to the second cap 160 which, in turn, can couple or "lock" the first cap 150 and the second cap 160 to one another. In FIG. 2C, the retaining surface 256 and the second surface 268 are shown as being spaced apart for the sake of illustration; those of ordinary skill in the art will understand that, in other embodiments, at least part of the retaining surface 256 can contact at least part of the second surface 268 to prevent, or at least partially prevent, the first cap 150 from moving relative to the second cap 160.

Referring to FIGS. 2A-2C together, to couple the dilator 130 to the valve 102, a user can position the locking members 252 of the first cap 150 such that the tabs 254 are at least partially aligned with the slots 264 of the second cap 160 and/or contacting the first surfaces 266 of the corresponding locking features 262. The user can then move the first cap 150 toward the second cap 160 to cause the tabs 254 to translate along the corresponding first surfaces 266 inwardly in a first direction D1 (FIG. 2C; e.g., toward the longitudinal axis X in FIG. 2A). The movement of the tabs 254 in the first direction D1 can cause a corresponding bend or deflection in the locking members 252. Continued movement of the first cap 150 toward the second cap 160 can move the tabs 254 past the corresponding first surfaces 266; once past the first surfaces 266, the locking members 252 can move in a second direction D2 (FIG. 2C; e.g., away from the longitudinal axis X in FIG. 2A) opposite the first direction D1. The movement of the locking members 252 in the second direction D2 can be due at least partially to the elastic or generally elastic deformation properties of the locking members 252. As the locking members 252 move in the second direction D2, each of the retaining surfaces 256 can be at least partially aligned with the second surface 268 of the corresponding locking features 262 to secure the first cap 150 and the second cap 160. That is, the tabs 254 can be advanced past and snap inward behind the corresponding second surfaces 268, which retain the tabs 254 and the first cap 150 in the locked position, e.g., as described previously herein.

Figures 3A, 3B:
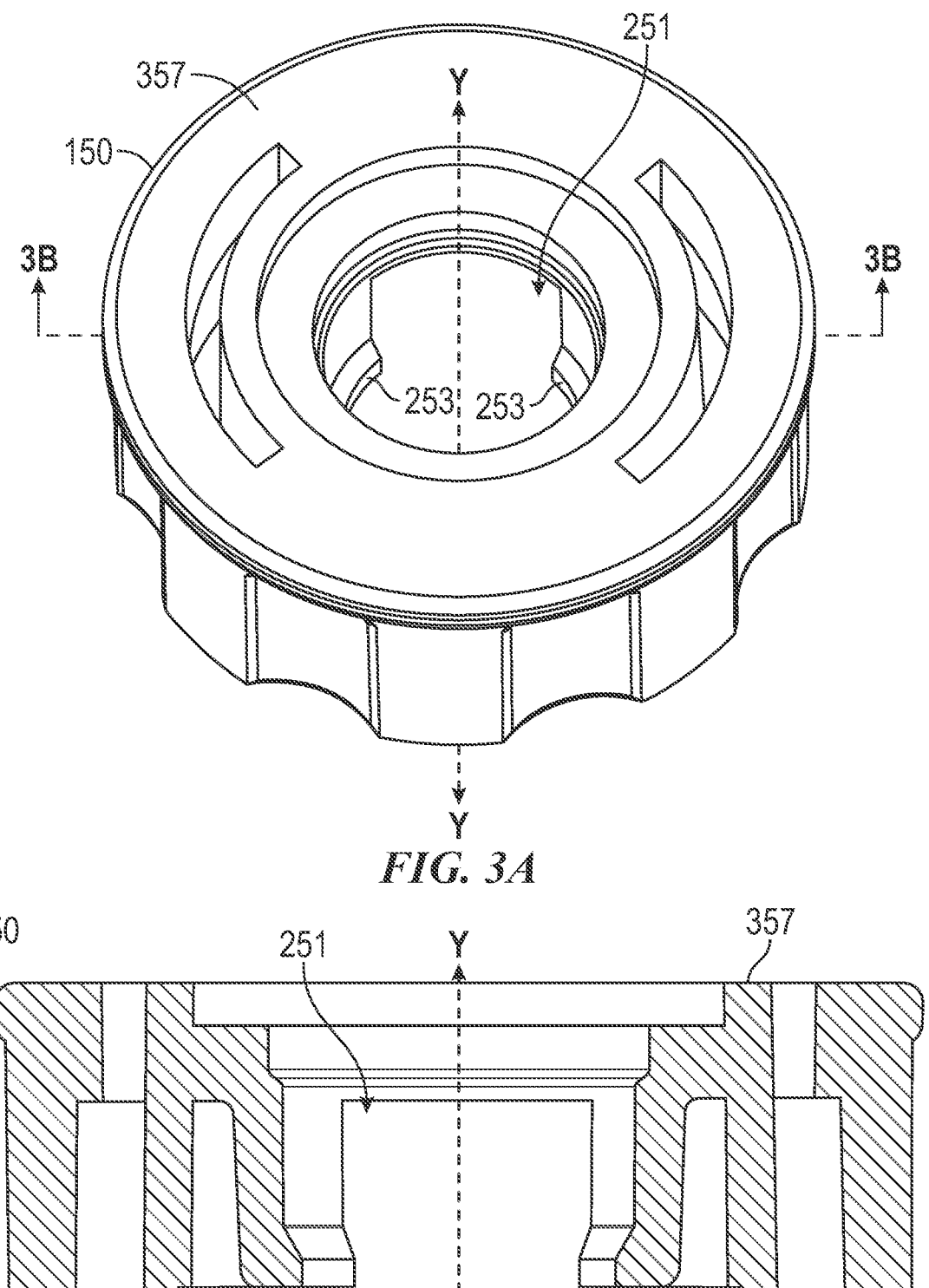
FIGS. 3A-3C are a perspective view, a cross-sectional view, and a bottom view, respectively, of a first cap of the cap assembly of FIG. 1 in accordance with embodiments of the present technology.
Figure 3C:
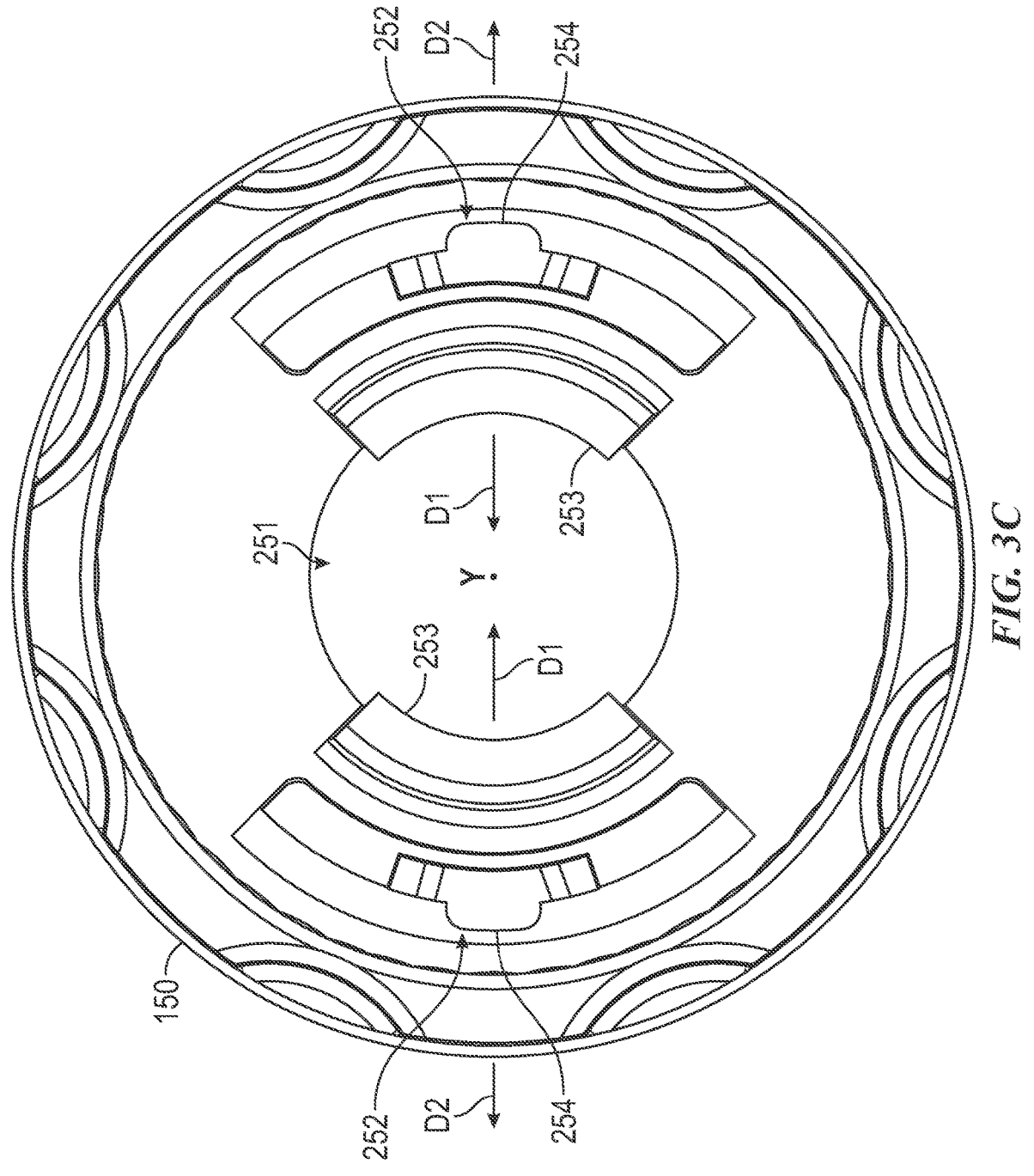

FIGS. 3A-3C are a perspective view, a cross-sectional view, and a bottom view, respectively, of the first cap 150 in accordance with embodiments of the present technology. Referring to FIGS. 3A-3C together, the first cap 150 can have a longitudinal axis Y and, when the first cap 150 is coupled to the valve 102 and the catheter 120 (FIG. 1), the longitudinal axis Y can be the same as (e.g., colinear with) the longitudinal axis X (FIGS. 1 and 2A). In the illustrated embodiment, the first cap 150 is bilaterally and/or radially symmetric relative to the longitudinal axis Y. In other embodiments, the first cap 150 can be configured to have any other symmetry and/or be asymmetrical.

Referring to FIG. 3B, each of the locking members 252 can be deflectable at least in the first direction D1 (e.g., outwardly and/or away from the longitudinal axis Y). Each of the luer coupling members 253 can be oppositely deflectable compared to the locking members 252 (e.g., at least in the second direction D2). Each of the locking members 252 and/or the luer coupling members 253 can extend away from an upper surface 357 of the first cap 150 (e.g., downwardly and/or in a direction parallel or generally parallel to the longitudinal axis Y). Referring to FIG. 3C, each of the locking members 252 and/or the luer coupling members 253 can be curved or arcuate and extend at least partially around the longitudinal axis Y. In at least some embodiments, the curvature of one or more of the locking members 252 and/or the luer coupling members 253 is concentric with the opening 251.

Figure 4A:
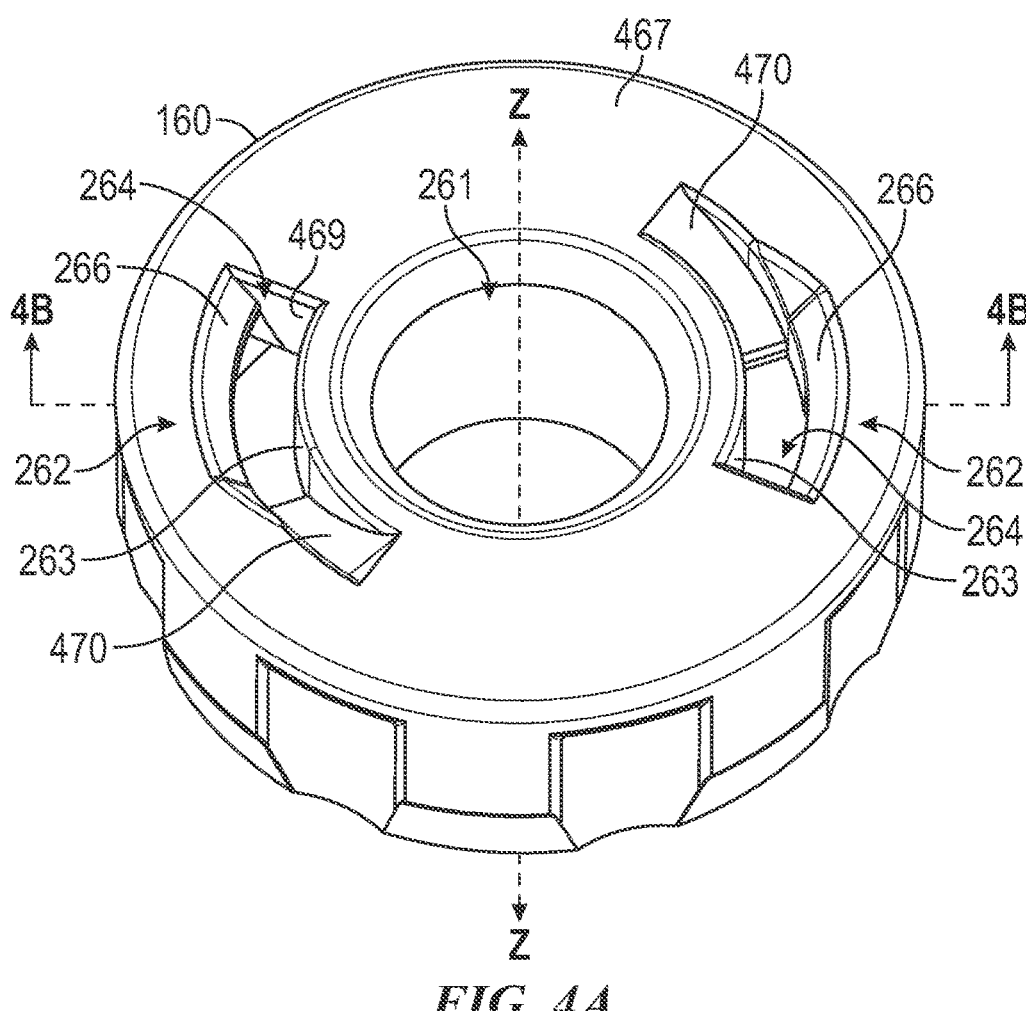
FIGS. 4A-4C are a perspective view, a cross-sectional view, and a bottom view, respectively, of a second cap of the cap assembly of FIG. 1 in accordance with embodiments of the present technology.
Figure 4B:
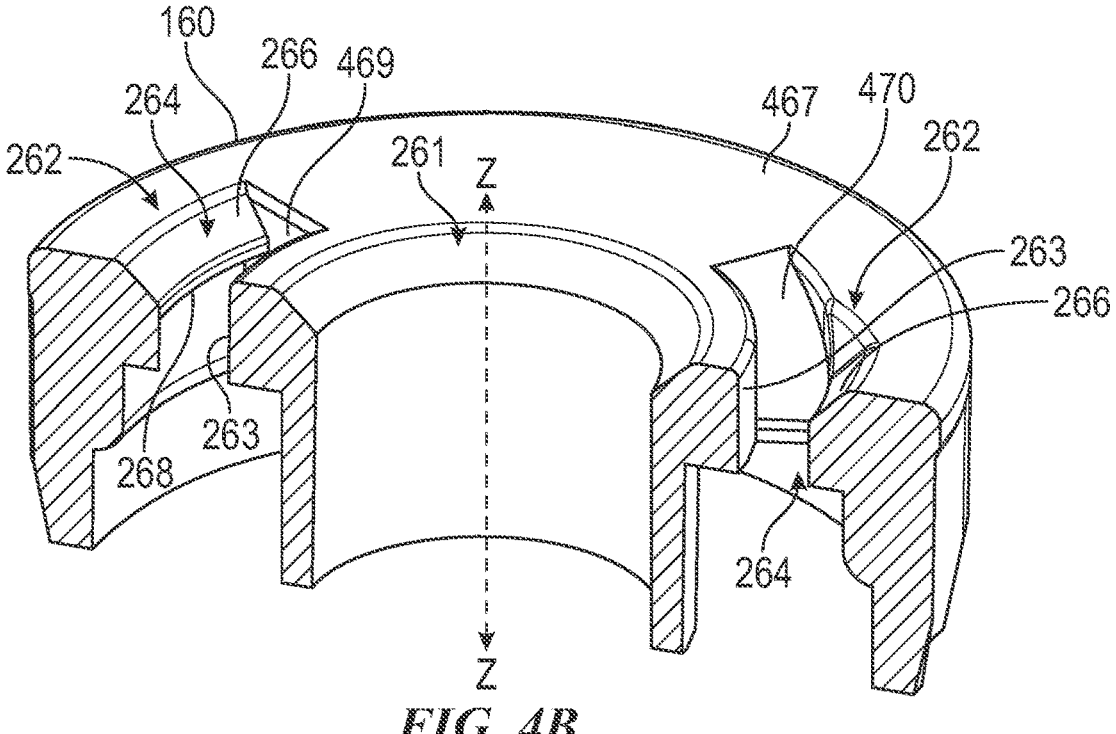
Figure 4C:
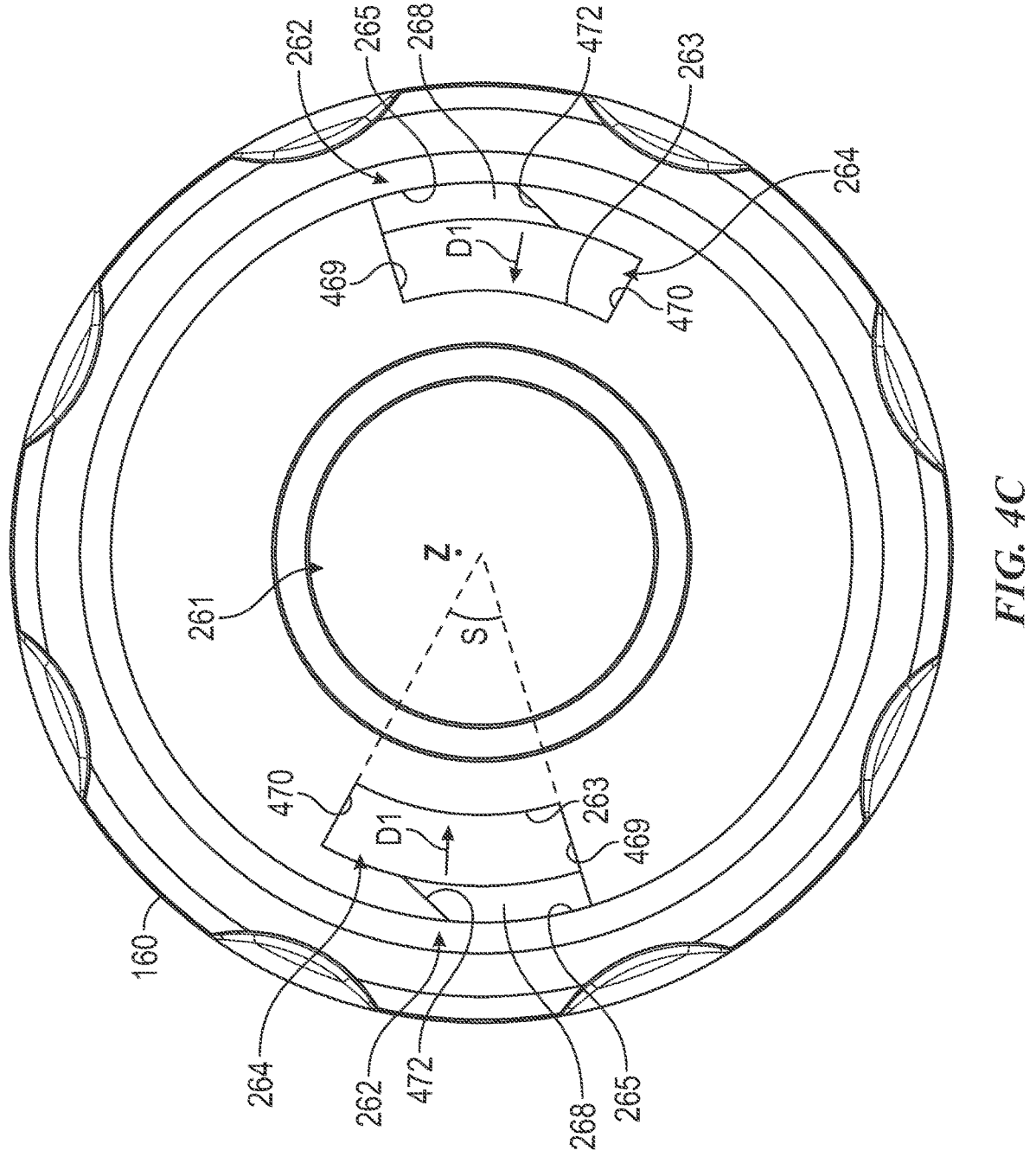

FIGS. 4A-4C are a perspective view, a cross-sectional view, and a bottom view, respectively, of the second cap 160 of the cap assembly 140 of FIG. 1 in accordance with embodiments of the present technology. Referring to FIGS. 4A-4C together, the second cap 160 can have a longitudinal axis Z and when the second cap 160 is coupled to the valve 102 and the catheter 120 (FIG. 1), the longitudinal axis Z can be the same as (e.g., colinear with) the longitudinal axis X (FIGS. 1 and 2A). Additionally, when the first cap 150 (FIGS. 1-3C) is coupled to the second cap 160, the longitudinal axis Z can be the same as (e.g., colinear with) the longitudinal axis Y (FIGS. 3A-3C). Each of the locking features 262 and/or one or more of the elements thereof (e.g., the slot 264, the first surface 266, etc.) can be curved or arcuate and extend at least partially around the longitudinal axis Z.

Referring to FIGS. 4A and 4B together, each of the locking features 262 can include an axial removal surface 470. Each of the axial removal surfaces 470 can be adjacent to the slot 264, opposite an end wall 469 of the slot 264 and at least partially between the first surface 266 and the inner wall 263. Additionally, each of the axial removal surfaces 470 can be inclined upwardly (e.g., along the longitudinal axis Z and/or toward an upper surface 467 of the second cap 160). Accordingly, when the locking members 252 are positioned in the slots 264, the axial removal surfaces 470 can drive the locking members 252 axially and/or upwardly there along, as described in detail below with reference to FIGS. 5A and 5B.

Referring to FIG. 4C, each of the locking features 262 can further include a radial removal surface 472. Each of the radial removal surfaces 472 can be positioned at least partially within the associated slot 264 and extend (e.g., downwardly, distally) from the associated second surface 268 (from the perspective shown in FIG. 4C, the radial removal surfaces 472 extend away from the page toward the viewer). Additionally, each of the radial removal surfaces 472 can be angled relative to the outer wall 265 and/or the inner wall 263. In the illustrated embodiment, for example, each of the radial removal surfaces 472 extend inward away from the outer wall 265 and toward the inner wall 263 and/or the longitudinal axis Z. Accordingly, when the locking members 252 are positioned in the slots 264 and brought into contact with the radial removal surfaces 472, the radial removal surfaces 472 can drive the locking members 252 inwardly there along, as described in detail below with reference to FIGS. 5A and 5B.

The slots 264 can have a slot dimension S defined at least partially by the slot end wall 469 and the axial removal surface 470. The slot dimension S can be an angle, an arc length, or any other suitable dimension. Because the locking members 252 can be inserted along the length of the slot 264, an increased slot dimension S can reduce the difficulty of aligning the first cap 150 with the second cap 160. Additionally, or alternatively, the slot dimension S can at least partially define an amount that the first cap 150 can rotate while at least partially coupled to the second cap 160. For example, a relatively high slot dimension (e.g., a greater arc length) can correspond to a relatively increased degree of rotation of the first cap 150, and a relatively low slot dimension can correspond to a relatively decreased degree of rotation of the first cap 150.

Figure 5A:
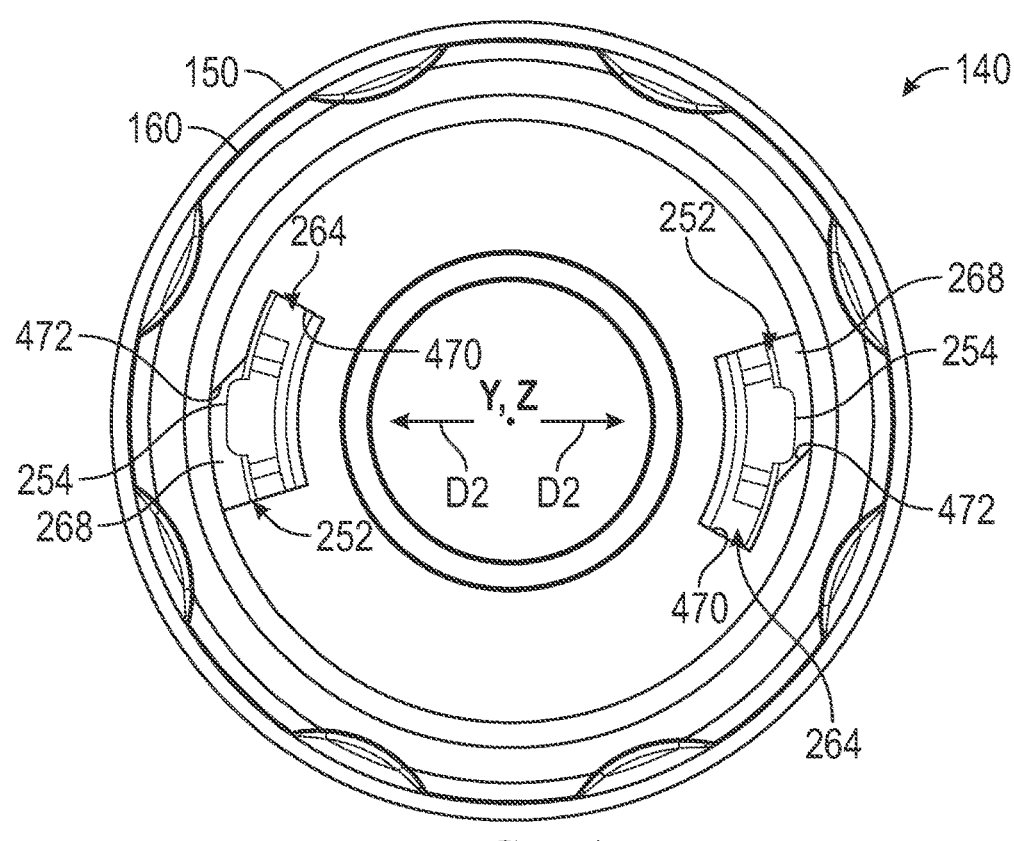
FIGS. 5A and 5B are respective bottom views of the cap assembly of FIG. 1 in accordance with embodiments of the present technology.
Figure 5B:
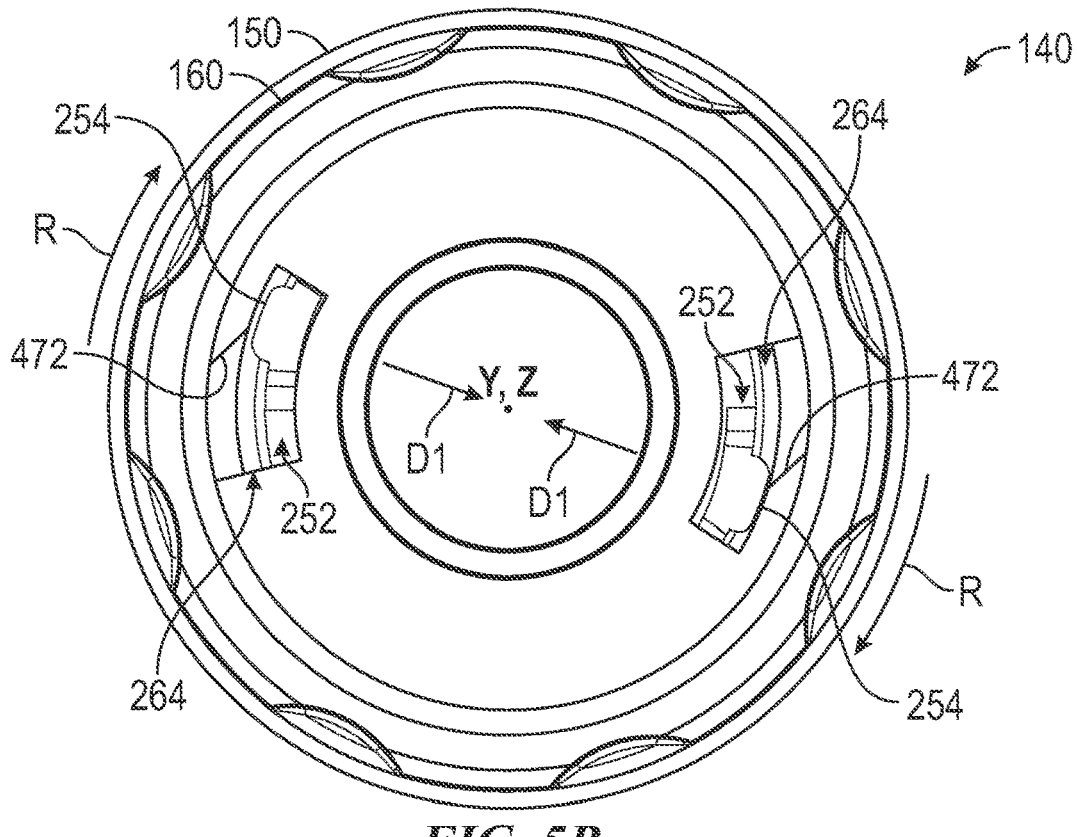

FIGS. 5A and 5B are respective bottom views of the cap assembly of FIG. 1 in accordance with embodiments of the present technology. In FIG. 5A, the cap assembly 140 is in the locked position with the locking members 252 of the first cap 150 positioned in the corresponding locking features 262 of the second cap 160 such that the first cap 150 is coupled to the second cap 160. In FIG. 5B, the cap assembly 140 is in the unlocked position in which the first cap 150 has been rotated in a direction R relative to the second cap 160 and/or about the longitudinal axes Y and/or Z to uncouple the first cap 150 from the second cap 160. In the illustrated embodiment, the direction R is a clockwise direction when viewed from the bottom of the cap assembly 140 (e.g., a counter-clockwise direction when viewed from the top of the cap assembly 140). In other embodiments, the first cap 150 and/or the second cap 160 can be configured such that the direction R is a counter-clockwise direction when viewed from the bottom of the cap assembly 140 (e.g., a clockwise direction when viewed from the top of the cap assembly 140).

Referring to FIGS. 5A and 5B together, rotating the first cap 150 in the direction R (FIG. 5B) can move the tabs 254 toward the corresponding radial removal surfaces 472 until one or more of the tabs 254 at least partially contact the corresponding radial removal surface 472. In response to the rotation in the direction R, the radial removal surfaces 472 can deflect each of the tabs 254 inward in the direction D1, as shown in FIG. 5B. This deflection of the tabs 254 causes a corresponding inward deflection in the associated locking members 252. In some aspects of the present technology, the radial removal surfaces 472 at least partially prevent the first cap 150 from being accidentally or unintentionally disconnected from the second cap 160 until a force (e.g., torque) sufficient to deflect the locking members 252 inward is applied to the first cap 150.

With the tabs 254 in the position shown in FIG. 5B, continued rotation of the first cap 150 in the direction R causes the tabs 254 to contact the corresponding axial removal surfaces 470 (FIGS. 4A and 4B). Each of the locking members 252 can translate upwardly across the corresponding axial removal surface 470 and cause the first cap 150 to move away from the second cap 160 in a direction generally along the longitudinal axis Z (e.g., to the unlocked position shown in FIG. 2A). Continued rotation of the first cap 150 can fully uncouple the first cap 150 and the second cap 160. However, it will be appreciated that, with the tabs 254 deflected inwardly in the position shown in FIG. 5B, the first cap 150 can be moved away from the second cap 160 without further rotation to decouple the first cap 150 from the second cap 160.

Accordingly, in some aspects of the present technology the locking features 262 include (i) the insertion surface 266 for deflecting one or more of the tabs 254 inward during insertion and/or in response to axial movement, (ii) the radial removal surface 472 for deflecting the tabs 254 inward (e.g., radially inward) during removal and/or in response to rotary movement, and (iii) the axial removal surface 470 for moving the tabs 254 upward (e.g., axially upward) during removal and/or in response to rotary movement. The insertion surface 266 can be positioned to align with the corresponding tab 254 when the cap assembly 140 is in the unlocked position. During insertion, the tab 254 can move toward, contact, and translate inwardly along the insertion surface 266. The radial removal surface 472 can be positioned proximate the tab 254 when the cap assembly 140 is in the locked position. During removal, the tab 254 can move (e.g., rotate) toward, contact, and translate inwardly along the radial removal surface 472. The cap assembly 140 can transition from the locked position toward the unlocked position as the tab 254 translates along the radial removal surface 472. Additionally, the tab 254 can move toward the axial removal surface 470 as it translates along the radial removal surface 472. The axial removal surface 470 can be angled upwardly, away from the radial removal surface 472. Accordingly, during removal, the tab 254 can move (e.g., rotate) toward, contact, and translate upward along the axial removal surface 470. Translating the tab 254 along the axial removal surface 470 can return the cap assembly 140 to the unlocked position.

Figure 6A:
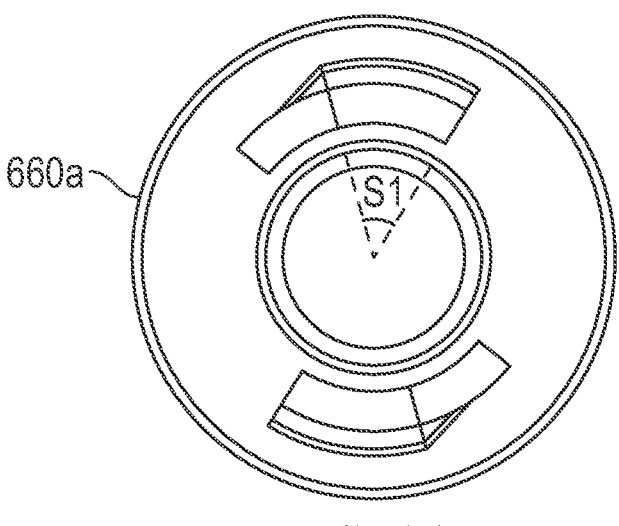
FIGS. 6A-6C are top views of respective second caps in accordance with additional embodiments of the present technology.
Figure 6B:
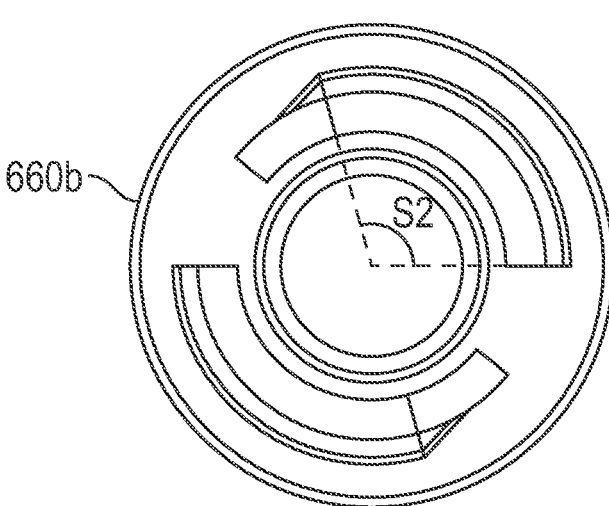
Figure 6C:
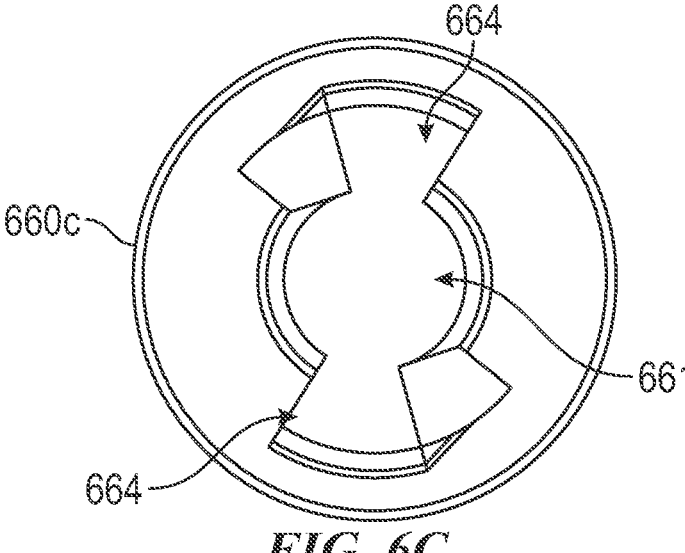

FIGS. 6A-6C are top views of respective second caps in accordance with additional embodiments of the present technology. Each of the second caps 660a-c can be generally similar to the second cap 160 of FIGS. 1-2C and 4A-5B. However, referring to FIG. 6A, the second cap 660a includes a reduced slot dimension S1, such that the second cap 660a does not allow the first cap (not shown) to rotate while remaining coupled to the second cap 660a and/or any rotation of the first cap begins the decoupling process described above. Referring to FIG. 6B, the second cap 660b includes an increased slot dimension S2 that allows the first cap (not shown) to rotate up to 60 degrees relative to the second cap 660b while still remaining coupled to the second cap 660b and/or before the rotation of the first cap begins the decoupling process described above. Referring to FIG. 6C, the second cap 660c does not include one or more of inner walls 263 (FIGS. 2B, 2C, and 4A-4C), such that the opening 661 and one or more of the slots 664 are connected or are otherwise not separated by inner walls.

Figure 7:
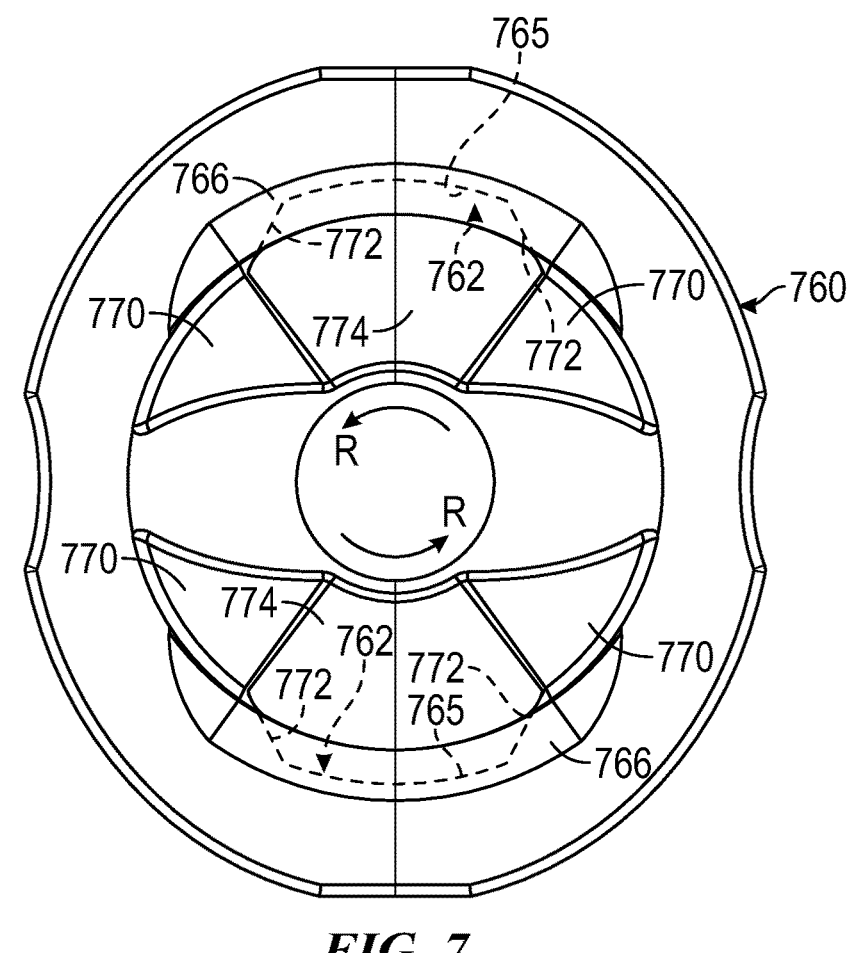
FIG. 7 is a top view of a second cap in accordance with additional embodiments of the present technology.

FIG. 7 is a top view of a second cap 760 configured in accordance with additional embodiments of the present technology. At least some aspects of the second cap 760 can be at least generally similar or identical in structure and/or function to one or more of the second caps 160, 660a-c described in detail previously herein. In the illustrated embodiment, the second cap 760 further includes one or more rotationally agnostic locking features 762 ("locking features 762"). In the illustrated embodiment, each of the locking features 762 includes an outer wall 765 and two radial removal surfaces 772 positioned e.g., on left and right sides of the outer wall 765. The second cap 760 can further include axial removal surfaces 770 positioned on the left and right sides of the locking features 762 and/or aligned with the radial removal surfaces 772 thereof. Accordingly, when a locking member of a first cap (e.g., the locking members 252 of the first cap 150 of FIG. 2A) is received within one of the locking features 762, the first cap can be rotated in the direction R or opposite the direction R (e.g., counterclockwise or clockwise) to drive the locking member against one of the radial removal surfaces 772 and uncouple the first cap and the second cap 760. Continued rotation of the first cap can translate the locking members of the first cap along the axial removal surfaces 770. This rotationally agnostic configuration of the locking features 762 is expected to allow the first cap to be quickly and easily uncoupled from the second cap 760. The locking features 762 can be aligned with and/or positioned distally of a respective first surface 766, and the locking members of a first cap (e.g., the locking members 252 of the first cap 150 of FIG. 2A) can contact and be driven radially inward by the first surfaces 766 to couple with the locking features 762.

In some embodiments, the second cap 760 can include one or more support surfaces 774 positioned radially inward of one of the first surfaces 766, e.g., between the axial removal surfaces 770 associated with one of the locking features 762. Each of the support surfaces 774 can be configured to contact at least part of a coupling member of a first cap, e.g., after the first cap is coupled/locked to the second cap 760. In some embodiments, one or more of the support surfaces 774 can be curved or concave. Accordingly, when the first cap is coupled to the second cap 760 and/or the coupling members of the first cap contact the support surfaces 774, the curvature/concavity of the support surfaces 774 can at least partially prevent rotation of the first cap relative to the second cap 760, e.g., in addition to or in lieu of the resistance to rotation of the first cap provided by the radial removal surfaces 772.

Figure 8:
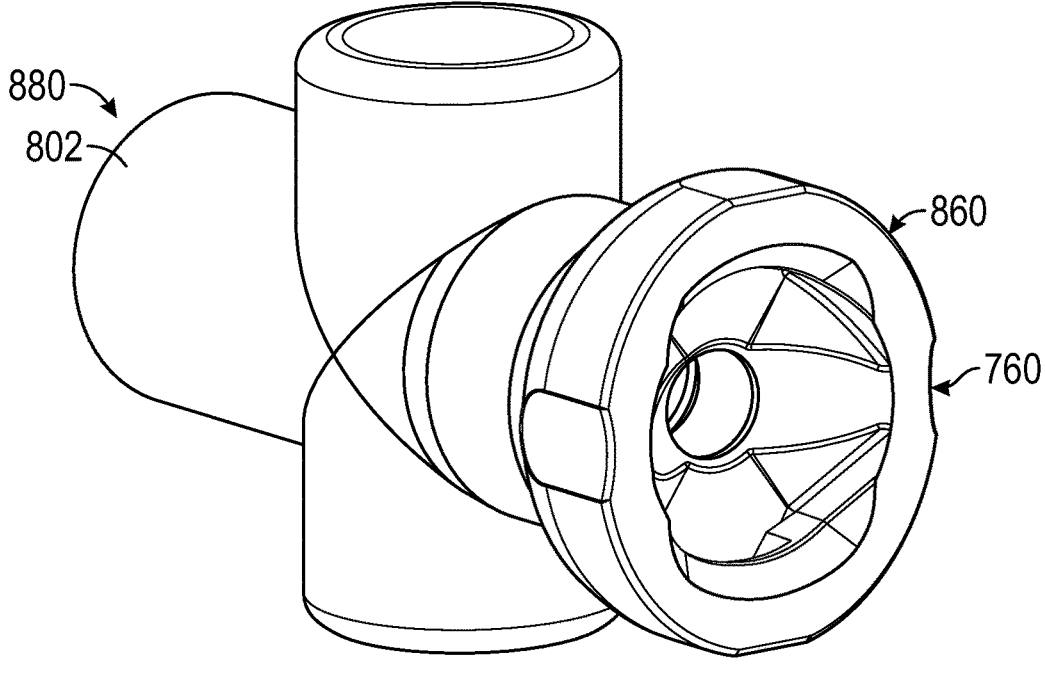
FIG. 8 is a perspective view of a cap-locking valve in accordance with embodiments of the present technology.

FIG. 8 is a perspective view of a cap-locking valve 880 configured in accordance with embodiments of the present technology. The cap-locking valve 880 can include a valve 802 and an integrated locking feature 860. The valve 802 can include at least some aspects that are at least generally similar or identical in structure and/or function to the valve 102 of FIG. 1. In at least some embodiments, for example, the valve 802 can be a hemostasis valve that is configured to maintain hemostasis during a clot removal procedure by preventing fluid flow in a proximal direction through the valve 802 as various components such as dilators, delivery sheaths, pull members, guidewires, interventional devices, other aspiration catheters, and so on are inserted through the valve 802.

The integrated locking feature 860 can be formed in the valve at or near a proximal end of the valve 802 or at another suitable position on/in the valve 802. The integrated locking feature 860 can include at least some aspects that are at least generally similar or identical in structure and/or function to one or more of the second caps 160, 660*a-c*, 760 described herein. In the illustrated embodiment, for example, the integrated locking feature 860 includes at least some features that are at least generally similar in structure and/or function to the second cap 760 of FIG. 7. In other embodiments, the integrated locking feature 860 can have another suitable configuration. In these and other embodiments, the integrated locking feature 860 can be directly integrated into the valve 802 rather than being included in a separate cap or other component releasably couplable to the valve 802.

Several aspects of the present technology are set forth in the following examples:

1. A cap assembly for a catheter, the cap assembly comprising:
   a first cap including a locking member, wherein the locking member includes an end portion and a tab positioned proximate the end portion; and
   a second cap including a locking feature, wherein the locking feature includes a slot extending at least partially through the second cap, and wherein
   the first cap is configured to be secured to the second cap in a locked position,
   in the locked position, the locking feature is configured to receive the locking member through the slot such that the tab engages a portion of the second cap to inhibit movement of the first cap relative to the second cap, and
   the first cap is configured to rotate relative to the second cap to move the tab out of engagement with the second cap to move the first cap from the locked position to an unlocked position.

2. The cap assembly of example 1 wherein the first cap includes an upper surface, and wherein the locking member extends from the upper surface in a direction generally perpendicular to the upper surface, and wherein the end portion of the locking member is opposite the upper surface.

3. The cap assembly of example 1 or example 2 wherein the tab extends perpendicularly from the locking member.

4. The cap assembly of any one of examples 1-3 wherein the tab defines a retaining surface positioned to contact at least a portion of the second cap when the first cap is coupled to the second cap.

5. The cap assembly of any one of examples 1~4 wherein the locking member is flexible, and wherein the second cap is configured to bend the locking member when the first cap moves between the unlocked position and the locked position.

6. The cap assembly of any one of examples 1-5 wherein the locking feature includes a locking surface positioned to at least partially contact the tab of the locking member when the first cap is coupled to the second cap.

7. The cap assembly of any one of examples 1-6 wherein the locking feature includes an angled insertion surface positioned to engage and deflect the locking member when the first cap moves from the unlocked position toward the locked position.

8. The cap assembly of example 7 wherein the cap assembly includes a longitudinal axis, and where the insertion surface is angled to bend the locking member inward toward the longitudinal axis.

9. The cap assembly of any one of examples 1-8 wherein the locking feature includes a radial removal surface, and wherein the radial removal surface is angled to deflect the tab inward when the first cap is rotated relative to the second cap.

10. The cap assembly of any one of examples 1-9 wherein the locking feature includes an axial removal surface positioned proximate the slot and angled to move the first cap away from the second cap when the first cap is rotated relative to the second cap.

11. The cap assembly of any one of examples 1-10 wherein:
    the first cap includes an upper surface, and the locking member extends from the upper surface in a direction perpendicular to the upper surface;
    the locking member is flexible and configured to deflect when the first cap moves between the unlocked position and the locked position;
    the tab defines a retaining surface positioned to contact at least a portion of the second cap in the locked position; and
    the locking feature includes
       a locking surface positioned to at least partially contact the retaining surface of the tab in the locked position,
       an insertion surface positioned to be at least partially aligned with the locking member and angled to deflect the locking member inward when the first cap moves from the unlocked position toward the locked position,
       a radial removal surface positioned proximate the tab of the locking member in the locked position, wherein the radial removal surface is angled to move the tab radially inward when the first cap moves from the locked position toward the unlocked position, and
       an axial removal surface positioned proximate the slot and angled to move the first cap longitudinally away from the second cap when the first cap moves from the locked positioned toward the unlocked position.

12. The cap assembly of any one of examples 1-11 wherein the locking member is a first locking member, wherein the locking feature is a first locking feature, wherein the first cap includes one or more second locking members, wherein the second cap includes one or more second locking features, and wherein individual ones of the second locking members are configured to receive and secure corresponding ones of the second locking members in the locked position.

13. The cap assembly of any one of examples 1-12 wherein the locking feature is configured to be rotationally agnostic such that rotation of the first cap relative to the second cap in a first direction and a second direction opposite the first direction moves the tab out of engagement with the second cap to move the first cap from the locked position to an unlocked position.

14. A vascular access system, comprising:
a valve having a proximal end and a distal end;
a catheter defining a lumen and coupled to the distal end of the valve, the catheter defining a longitudinal axis of the vascular access system;
a dilator configured to extend at least partially through the valve and the lumen; and
a cap assembly movable between a locked configuration and an unlocked configuration,
wherein the cap assembly includes (i) a valve cap connected to the proximal end of the valve and including a coupling feature, and (ii) a dilator cap coupled to the dilator and including a coupling tab insertable into the coupling feature, wherein—
in the locked configuration, the coupling feature is configured to receive the coupling tab such that the coupling tab engages a portion of the valve cap to inhibit movement of the dilator relative to the valve along the longitudinal axis, and
the dilator cap is configured to rotate relative to the valve cap to move the coupling tab out of engagement with the valve cap to move the cap assembly from the locked configuration toward the unlocked configuration.

15. The vascular access system of example 14 wherein the coupling tab is flexible, wherein the coupling feature is configured to deflect the coupling tab toward the longitudinal axis when the cap assembly moves from the unlocked configuration toward the locked configuration.

16. The vascular access system of example 14 or example 15 wherein the dilator cap includes a coupling member extending in a direction generally parallel to the dilator and having a distal end, and wherein the coupling tab is positioned proximate the distal end of the coupling member.

17. The vascular access system of any one of examples 14-16 wherein valve cap has a valve cap longitudinal axis, and wherein the coupling feature is curved circumferentially at least partially about the valve cap longitudinal axis.

18. The vascular access system of any one of examples 14-17 wherein the coupling feature includes a coupling surface positioned to at least partially contact the coupling tab of the dilator cap when the cap assembly is in the locked configuration.

19. The vascular access system of example 18 wherein the coupling feature includes an insertion surface positioned to engage and deflect the coupling tab toward the longitudinal axis when the cap assembly moves from the unlocked configuration toward the locked configuration.

20. The vascular access system of example 19 wherein the insertion surface is positioned proximally from the coupling surface.

21. The vascular access system of example 19 or example 20 wherein the insertion surface forms an acute interior angle relative to the coupling surface.

22. The vascular access system of any one of examples 14-21 wherein the coupling feature includes a radial removal surface configured to move the coupling tab radially inward toward the longitudinal axis when the cap assembly moves from the locked configuration toward the unlocked configuration.

23. The vascular access system of any one of examples 14-22 wherein the coupling feature includes (i) a slot configured to receive the coupling tab, and (ii) an axial removal surface positioned proximate the slot and angled to move the dilator cap away from the valve cap along the longitudinal axis when the dilator cap is rotated relative to the valve cap.

24. The vascular access system of any of examples 14-22 wherein the coupling feature includes an outer wall and a pair of radial removal surfaces positioned on left and right sides of the outer wall, and wherein—
in the locked configuration, the coupling tab is positioned between the pair of radial removal surfaces, and
rotation of the dilator cap in a left or right direction relative to the valve cap moves the cap assembly from the locked configuration toward the unlocked configuration.

25. The vascular access system of any one of examples 14-24 wherein the valve cap is integrally formed with proximal end of the valve.

26. The vascular access system of any one of examples 14-24 wherein the valve cap is releasably coupled to the proximal end of the valve.

27. A method of using a vascular access system, the method comprising:
aligning a first cap of the vascular access system with a second cap of the vascular access system, wherein the first cap is coupled to a dilator of the vascular access system, wherein the second cap is coupled to a catheter of the vascular access system, and wherein aligning the first cap with the second cap includes aligning at a locking member of the first cap with a locking feature of the second cap; and
coupling the first cap to the second cap to inhibit the dilator from moving relative to the catheter of the vascular access system, wherein coupling the first cap to the second cap includes inserting the locking member into the locking feature such that the locking feature drives the locking member past a locking surface of the locking feature, and wherein the locking surface is configured to engage the locking member to inhibit longitudinal movement of the first cap relative to the second cap.

28. The method of example 27 wherein coupling the first cap to the second cap further includes positioning the dilator at least partially within the catheter.

29. The method of example 27 or example 28 wherein coupling the first cap to the second cap further includes inserting the dilator fully through the catheter.

30. The method of any one of examples 27-29 wherein aligning the locking member of the first cap with the locking feature of the second cap includes aligning a tab of the locking member with an insertion surface of the locking feature.

31. The method of example 30 wherein moving the first cap toward the second cap includes (i) positioning the tab of the locking member to contact the insertion surface of the locking feature and (ii) translating the tab across the insertion surface to deflect the tab.

32. The method of any one of examples 27-31, further comprising rotating the first cap relative to the second cap to uncouple the first cap from the second cap after coupling the first cap to the second cap.

33. The method of example 32 wherein rotating the first cap includes translating at least a portion of the locking member across a radial removal surface of the locking feature, wherein the radial removal surface is angled to deflect the locking member when the first cap is rotated relative to the second cap.

34. The method of example 32 or example 33 wherein rotating the first cap includes moving the first cap longitudinally away from the second cap.

35. The method of example 34 wherein moving the first cap away from the second cap includes translating the locking member across an axial removal surface of the locking feature, wherein the axial removal surface is angled to move the first cap away from the second cap as the locking member translates across the axial removal surface.

36. The method of any one of examples 32-35 wherein rotating the first cap relative to the second cap to uncouple the first cap from the second cap includes rotating the first cap in a first direction or a second direction opposite the first direction to uncouple the first cap from the second cap.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A cap assembly for a catheter, the cap assembly comprising:
   a first cap including a locking member, wherein the locking member includes an end portion and a tab positioned proximate the end portion; and
   a second cap defining a longitudinal axis and including a locking feature, wherein the locking feature includes a slot extending at least partially through the second cap and an axial removal surface positioned proximate the slot, sloped relative to the longitudinal axis, and extending at least partially around the longitudinal axis, and wherein
   the first cap is configured to be secured to the second cap in a locked position,
   in the locked position, the second cap is configured to receive the locking member through the slot such that the tab engages a portion of the second cap to inhibit movement of the first cap relative to the second cap, and
   the first cap is configured to rotate relative to the second cap to (i) move the tab out of engagement with the portion of the second cap and thereby move the first cap from the locked position to an unlocked position and to (ii) translate the tab along at least a portion of the axial removal surface to drive the first cap longitudinally away from the second cap.

2. The cap assembly of claim 1 wherein the first cap includes an upper surface, and wherein the locking member extends from the upper surface in a direction generally perpendicular to the upper surface, and wherein the end portion of the locking member is opposite the upper surface.

3. The cap assembly of claim 1 wherein the tab extends perpendicularly from the locking member.

4. The cap assembly of claim 1 wherein the tab defines a retaining surface positioned to contact at least a portion of the second cap when the first cap is coupled to the second cap.

5. The cap assembly of claim 1 wherein the locking member is flexible, and wherein the second cap is configured to bend the locking member when the first cap moves between the unlocked position and the locked position.

6. The cap assembly of claim 1 wherein the locking feature includes a locking surface positioned to at least partially contact the tab of the locking member when the first cap is coupled to the second cap.

7. The cap assembly of claim 1 wherein the locking feature includes an angled insertion surface positioned to engage and deflect the locking member when the first cap moves from the unlocked position toward the locked position.

8. The cap assembly of claim 7 wherein the cap assembly includes a longitudinal axis, and where the insertion surface is angled to bend the locking member inward toward the longitudinal axis.

9. The cap assembly of claim 1 wherein the locking feature includes a radial removal surface, and wherein the radial removal surface is angled to deflect the tab inward when the first cap is rotated relative to the second cap.

10. The cap assembly of claim 1 wherein:
    the first cap includes an upper surface, and the locking member extends from the upper surface in a direction perpendicular to the upper surface;
    the locking member is flexible and configured to deflect when the first cap moves between the unlocked position and the locked position;

the tab defines a retaining surface positioned to contact at least a portion of the second cap in the locked position; and the locking feature includes a locking surface positioned to at least partially contact the retaining surface of the tab in the locked position, an insertion surface positioned to be at least partially aligned with the locking member and angled to deflect the locking member inward when the first cap moves from the unlocked position toward the locked position, and a radial removal surface positioned proximate the tab of the locking member in the locked position, wherein the radial removal surface is angled to move the tab radially inward when the first cap moves from the locked position toward the unlocked position.

11. The cap assembly of claim 1 wherein the locking member is a first locking member, wherein the locking feature is a first locking feature, wherein the first cap includes one or more second locking members, wherein the second cap includes one or more second locking features, and wherein individual ones of the second locking members are configured to receive and secure corresponding ones of the second locking members in the locked position.

12. The cap assembly of claim 1 wherein the locking feature is configured to be rotationally agnostic such that rotation of the first cap relative to the second cap in a first direction and a second direction opposite the first direction moves the tab out of engagement with the second cap to move the first cap from the locked position to the unlocked position.

13. A vascular access system, comprising:

a valve having a proximal end and a distal end;

a catheter defining a lumen and coupled to the distal end of the valve, the catheter defining a longitudinal axis of the vascular access system;

a dilator configured to extend at least partially through the valve and the lumen; and a cap assembly movable between a locked configuration and an unlocked configuration, wherein the cap assembly includes (i) a valve cap connected to the proximal end of the valve and including a coupling feature, and (ii) a dilator cap coupled to the dilator and including a coupling tab insertable into the coupling feature, wherein the coupling feature includes an angled insertion surface and a slot extending from the angled insertion surface through at least a portion of the valve cap, the angled insertion surface is positioned to engage and deflect the coupling tab as the dilator cap is moved axially toward the valve cap to transition the cap assembly from the unlocked configuration toward and/or to the locked configuration, in the locked configuration, the coupling feature is configured to receive the coupling tab such that the coupling tab engages a portion of the valve cap through the slot to inhibit movement of the dilator relative to the valve along the longitudinal axis, and the dilator cap is configured to rotate relative to the valve cap to move the coupling tab out of engagement with the valve cap to move the cap assembly from the locked configuration toward the unlocked configuration.

14. The vascular access system of claim 13 wherein the coupling tab is flexible, wherein the coupling feature is configured to deflect the coupling tab toward the longitudinal axis when the cap assembly moves from the unlocked configuration toward the locked configuration.

15. The vascular access system of claim 13 wherein the dilator cap includes a coupling member extending in a direction generally parallel to the dilator and having a distal end, and wherein the coupling tab is positioned proximate the distal end of the coupling member.

16. The vascular access system of claim 13 wherein the valve cap has a valve cap longitudinal axis, and wherein the coupling feature is curved circumferentially at least partially about the valve cap longitudinal axis.

17. The vascular access system of claim 13 wherein the coupling feature includes a coupling surface positioned to at least partially contact the coupling tab of the dilator cap when the cap assembly is in the locked configuration.

18. The vascular access system of claim 17 wherein the angled insertion surface is positioned proximally from the coupling surface.

19. The vascular access system of claim 17 wherein the angled insertion surface forms an acute interior angle relative to the coupling surface.

20. The vascular access system of claim 13 wherein the coupling feature includes a radial removal surface configured to move the coupling tab radially inward toward the longitudinal axis when the cap assembly moves from the locked configuration toward the unlocked configuration.

21. The vascular access system of claim 13 wherein the coupling feature includes (i) a slot configured to receive the coupling tab, and (ii) an axial removal surface positioned proximate the slot and angled to move the dilator cap away from the valve cap along the longitudinal axis when the dilator cap is rotated relative to the valve cap.

22. The vascular access system of claim 13 wherein the coupling feature includes an outer wall and a pair of radial removal surfaces positioned on left and right sides of the outer wall, and wherein in the locked configuration, the coupling tab is positioned between the pair of radial removal surfaces, and rotation of the dilator cap in a left or right direction relative to the valve cap moves the cap assembly from the locked configuration toward the unlocked configuration.

23. The vascular access system of claim 13 wherein the valve cap is integrally formed with the proximal end of the valve.

24. The vascular access system of claim 13 wherein the valve cap is releasably coupled to the proximal end of the valve.

25. A method of using a vascular access system, the method comprising:

aligning a first cap of the vascular access system with a second cap of the vascular access system, wherein the first cap is coupled to a dilator of the vascular access system, wherein the second cap is coupled to a catheter of the vascular access system, and wherein aligning the first cap with the second cap includes aligning a locking member of the first cap with a locking feature of the second cap, and aligning a tab of the locking member with an angled insertion surface of the locking feature; and coupling the first cap to the second cap to inhibit the dilator from moving relative to the catheter of the vascular access system, wherein coupling the first cap to the second cap includes positioning the tab of the locking member to contact the angled insertion surface of the locking feature, moving the first cap axially toward the second cap to translate the tab across the angled insertion surface, and inserting the locking member into the locking feature such that the locking feature drives the locking member past a locking surface of the locking feature, wherein the locking surface is configured to engage the locking member to inhibit longitudinal movement of the first cap relative to the second cap.

26. The method of claim 25 wherein coupling the first cap to the second cap further includes positioning the dilator at least partially within the catheter.

27. The method of claim 25 wherein coupling the first cap to the second cap further includes inserting the dilator fully through the catheter.

28. The method of claim 25, further comprising rotating the first cap relative to the second cap to uncouple the first cap from the second cap after coupling the first cap to the second cap.

29. The method of claim 28 wherein rotating the first cap includes translating at least a portion of the locking member across a radial removal surface of the locking feature, wherein the radial removal surface is angled to deflect the locking member when the first cap is rotated relative to the second cap.

30. The method of claim 28 wherein rotating the first cap includes moving the first cap longitudinally away from the second cap.

31. The method of claim 30 wherein moving the first cap away from the second cap includes translating the locking member across an axial removal surface of the locking feature, wherein the axial removal surface is angled to move the first cap away from the second cap as the locking member translates across the axial removal surface.

32. The method of claim 28 wherein rotating the first cap relative to the second cap to uncouple the first cap from the second cap includes rotating the first cap in a first direction or a second direction opposite the first direction to uncouple the first cap from the second cap.

* * * * *